US006232297B1

(12) United States Patent
Linden et al.

(10) Patent No.: US 6,232,297 B1
(45) Date of Patent: May 15, 2001

(54) METHODS AND COMPOSITIONS FOR TREATING INFLAMMATORY RESPONSE

(75) Inventors: Joel M. Linden; Gail W. Sullivan; Ian J. Sarembock; Timothy MacDonald; Mark Okusa, all of Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 09/333,387

(22) Filed: Jun. 15, 1999

Related U.S. Application Data

(60) Provisional application No. 60/118,029, filed on Feb. 1, 1999, provisional application No. 60/124,316, filed on Mar. 12, 1999, provisional application No. 60/133,374, filed on May 10, 1999, and provisional application No. 60/135,573, filed on May 24, 1999.

(51) Int. Cl.[7] .......................... A61K 31/70; C07H 19/16; C07H 19/167; C07H 19/173
(52) U.S. Cl. .................. 514/46; 536/27.22; 536/27.3; 536/27.6; 536/27.62
(58) Field of Search .................. 514/46; 536/27.22, 536/27.3, 27.6, 27.62

(56) References Cited

U.S. PATENT DOCUMENTS

| Re. 36,494 | 1/2000 | Olsson et al. ......................... 514/46 |
|---|---|---|
| 3,892,777 | 7/1975 | Gruenman et al. ................. 260/340.5 |
| 4,193,926 | 3/1980 | Schmiechen et al. ............... 260/326 |
| 4,242,345 | 12/1980 | Brenner et al. ...................... 424/253 |
| 4,665,074 | 5/1987 | Amschler ............................. 514/247 |
| 4,824,660 | 4/1989 | Angello et al. ...................... 424/1.1 |
| 4,879,296 | 11/1989 | Daluge et al. ....................... 514/263 |
| 4,938,949 | 7/1990 | Borch et al. ......................... 424/10 |
| 4,956,345 | 9/1990 | Miyasaka et al. ................... 514/46 |
| 4,965,271 | 10/1990 | Mandell et al. ..................... 514/263 |
| 5,070,877 | 12/1991 | Mohiuddin et al. ............... 128/653.4 |
| 5,096,906 | 3/1992 | Mandell et al. ..................... 514/263 |
| 5,124,455 | 6/1992 | Lombardo et al. .................. 546/181 |
| 5,140,015 | 8/1992 | Olsson et al. ........................ 514/46 |
| 5,189,027 | * 2/1993 | Miyashita et al. ................... 514/46 |
| 5,272,153 | 12/1993 | Mandell et al. ..................... 514/263 |
| 5,278,150 | 1/1994 | Olsson et al. ........................ 514/46 |
| 5,298,508 | 3/1994 | Jacobson et al. .................... 514/263 |
| 5,565,462 | 10/1996 | Eitan et al. .......................... 514/262 |
| 5,593,975 | 1/1997 | Cristalli .............................. 514/46 |
| 5,665,754 | 9/1997 | Feldman et al. ..................... 514/397 |
| 5,668,139 | 9/1997 | Belardinelli et al. ................ 514/263 |
| 5,696,254 | 12/1997 | Mansour et al. .................... 536/24.11 |
| 5,731,296 | 3/1998 | Sollevi ................................. 536/46 |
| 5,756,706 | 5/1998 | Mansour et al. .................... 536/27.11 |
| 5,854,081 | 12/1998 | Linden et al. ....................... 436/501 |
| 5,877,180 | 3/1999 | Linden et al. ....................... 514/266 |
| 5,932,558 | 8/1999 | Cronstein et al. ................... 514/46 |
| 5,998,386 | 12/1999 | Feldman .............................. 514/263 |
| 6,004,945 | 12/1999 | Fukunaga ........................... 514/46 |
| 6,020,321 | 2/2000 | Cronstein et al. ................... 514/46 |
| 6,020,339 | 2/2000 | Perrier et al. ....................... 514/269 |
| 6,034,089 | 3/2000 | Han et al. ............................ 514/269 |

FOREIGN PATENT DOCUMENTS

| 0700908 | 3/1996 | (EP) . |
|---|---|---|
| 9511681 | 5/1995 | (WO) . |
| 9604280 | 2/1996 | (WO) . |
| 9847509 | 10/1998 | (WO) . |
| 98/57651 | 12/1998 | (WO) . |
| 99/63938 | 12/1999 | (WO) . |

OTHER PUBLICATIONS

Andersson, P., et al., "Anti–anaphylactic and anti–inflammatory effects of xanthines in the lung", *Curr. Clin. Pract. Ser.*, , 187–192, (1985).

Berkich, D.A., et al., "Evidence of Regulated Coupling of A1 Adenosine Receptors by Phosphorylation in Zucker Rats.", *American Physiological Society*, 268(4 Pt 1), E693–E704, (Apr., 1995).

Bhattacharya, S., et al., "Effects of Long–term Treatment With the Allosteric Enhancer, PD81,723, on Chinese Hamster Ovary Cells Expressing Recombinant Human $A_1$ Adenosine Receptors", *Molecular Pharmacology*, 50(1), 104–111, (Jul., 1996).

Bhattacharya, S., et al., "The Allosteric Enhancer, PD 81,723, Stabilizes Human $A_1$ Adenosine Receptor Coupling to G Proteins", *Biochimica Biophysica Acta*, 1265(1), 15–21, (Feb. 1995).

Bridges, A.J., et al., "$N^6$–[2–(3, 5–Dimethoxyphenyl)–2–(2–Methylphenyl)–Ethyl]Adenosine and Its Uronamide Derivatives. Novel Adenosine Agonists With Both High Affinity and High Selectivity for the Adenosine $A_2$ Receptor", *Journal of Medicinal Chemistry*, 31(7), 1282–1285, (1988).

Buster, B., et al., "The Effect of Adenosine Receptor Agonists on Neutrophil Pleocytosis and Blood–Brain Barrier Pathophysiology in Experimental Bacterial Meningitis", *Abstract of the Interscience Conference on Antimicrobial Agents and Chemotherapy*, 37, 39, (1997).

Cembrzynska, N.M., et al., "Elevated Release of Tumor Necrosis Factor–alpha and Interferon–gamma by Bronchoalveolar Leukocytes From Patients With Bronchial Asthma.", *American Review of Respiratory Disease*, 147(2), 291–295, (1993).

Cothran, D.L., et al., "Ontogeny of Rat Myocardial $A_1$ Adenosine Receptors", *Biol Neonate*, 68(2), 111–118, (1995).

Cristalli, G., et al., "Alkynyl Derivatives of Adenosine an Adenosine–5'–N–ethyluronamide as Selective Agonists at $A_2$ Adenosine Receptors1", *Journal of Medicinal Chemistry*, 35(13), 2363–2368, (1992).

(List continued on next page.)

*Primary Examiner*—William R. A. Jarvis
(74) *Attorney, Agent, or Firm*—Schwegman, Lundberg, Woessner & Kluth, P.A.

(57) ABSTRACT

Compounds and methods are provided to treat inflammatory conditions with certain $A_{2A}$ adenosine receptor antagonists.

48 Claims, 9 Drawing Sheets

OTHER PUBLICATIONS

Cronstein, B.N., et al., "Adenosine Modulates the Generation of Superoxide Anion by Stimulated Human Neutrophils Via Interaction With a Specific Cell Surface Receptor", *Annals New York Academy of Science*, 451, 291–314, (1985).

Cronstein, B.N., et al., "Adenosine; A Physiologic Modulator Of Superoxide Anion Generated By Human Neutrophils. Adenosine Acts Via An $A_2$ Receptor On Human Neutrophils", *Journal of Immunology*, 135(2), 1366–1371, (1985).

Cronstein, B.N., et al., "Engagement of Adenosine Receptors Inhibits Hydrogen Peroxide ($H_2O_2$) Release by Activated Human Neutrophils", *Clinical Immunology and Immunopathology*, 42(1), 76–85, (1987).

Cronstein, B.N., et al., "Methotrexate Inhibits Leukocyte Influx Into Inflammatory Sites Via The Adenosine ($A_2$) Receptor", *Clinical Research*, 41(2), 244A, (1993).

Cronstein, B.N., et al., "The Adenosine/Neutrophil Paradox Resolved: Human Neutrophils Possess Both $A_1$ and $A_2$ Receptors That Promote Chemotaxis and Inhibits $O_2$ Generation, Respectively", *Journal of Clinical Investigation*, 85(4), 1150–1157, (1990).

Cronstein, N., et al., "Occupancy Of Adenosine Receptors Raises Cyclic AMP Alone And In Synergy With Occupancy Of Chemoattractant Receptors And Inhibits Membrane Depolarization", *Biochemical Journal*, 252(3), 709–715, (1988).

De La Harpe, J., et al., "Adenosine Regulates the Respiratory Burst Of Cytokine –Triggered Human Neutrophils Adherent To Biological Surfaces", *Journal of Immunology*, 143(2), 596–602, (1989).

Dinarello, C.A., "Interleukin–1 And Tumor Necrosis Factor: Effector Cytokines In Autoimmune Diseases", *Seminars in Immunology*, 4, 133–145, (1992).

Doyle, M.P., et al., "Nucleoside–induced Arteriolar Constriction: a Mast Cell–dependent Response.", *American Journal of Physiology*, H2042–H2050, (May, 1994).

Feoktistov, I., et al., "Adenosine $A_{2b}$ Receptors", *The American Society for Pharmacological and Experimental Therapeutics*, 49(4), 381–402, (1997).

Feoktistov, I., et al., "Role of Adenosine in Asthma", *Drug Development Research*, 39, 333–336, (1996).

Ferrante, A., et al., "Optimal Conditions for Simultaneous Purification of Mononuclear and Polymorphonuclear Leucocytes From Human Blood by the Hypaque–Ficoll Method", *Journal of Immunological Methods*, 36(2), 109, (1980).

Figler, R.A., et al., "Reconstitution of Bovine $A_1$ Adenosine Receptors and G Proteins in Phospholipid Vesicles: βγ–Subunit Composition Influences Guanine Nucleotide Exchange and Agonist Binding", *Biochemistry*, 36(51), 16288–16299, (1997).

Figler, R.A., et al., "Reconstitution of Recombinant Bovine $A_1$ Adenosine Receptors in Sf9 Cell Membranes with Recombitant G Proteins of Defined Composition.", *Molecular Pharmacology*, 50(6), 1587–1595, (Dec. 1996).

Firestein, G.S., et al., "Adenosine Regulating Agents: A Novel Approach to Inflammation and Inflammatory Arthritis", *Clinical Research*, 41(2), 170A, (1993).

Francis, J.E., et al., "Highly Selective Adenosine $A_2$ Receptor Agonists in a Series of N–Alkylated 2–Aminoadenosines", *Journal of Medicinal Chemistry*, 34(8), 2570–2579, (1991).

Gao, Z., et al., "$A_{2B}$ Adenosine and $P2Y_2$ Receptors Stimulate Mitogen–activated Protein Kinase in Human Embryonic Kidney–293 Cells. Cross–talk Between Cyclic AMP and Protein Kinase c Pathways", *Journal of Biological Chemistry*, 274(9), 5972–5980, (Feb. 1999).

Gao, Z., et al., "Purification of $A_1$ Adenosine Receptor–G–protein Complexes: Effects of Receptor Down–regulation and Phosphorylation on Coupling", *Biochemical Journal*, 338(Pt3), 729–736, (Mar., 1999).

Gilchrist, A., et al., "Antagonists of the Receptor–G Protein Interface Block $G_i$coupled Signal Transduction", *Journal of Biological Chemistry*, 273(24), 14912–14919, (Jun., 1998).

Glover, D.K., et al., "Pharmacological Stress Thallium Scintigraphy With 2–Cyclohexylmethylidenehydrazinoadenosine (WRC–0470) A Novel, Short–Acting Adenosine A2A Receptor Agonist.", *Circulation*, 94, 1726—1732, (1996).

Griswold, D.E., et al., "Effects of Selective Phosphodieasterase Type IV Inhibitor, Rolipram, on Fluid and Cellular Phases of Inflammatory Response", *Chemical Abstract*, 119, Abstract No. 173828e, (1993).

Hanlon, W.A., et al., "rTNFα Facilitate Human Polymorphonuclear Leukocyte Adherence to Fibrinogen Matrices With Mobilization of Specific and Tertiary But Not Azurophilic Granule Markers", *Journal of Leukocyte Biology*, 50(1), 43–48, (1991).

Holmes, et al., "Restenosis After Percutaneous Transluminal Coronary Angioplasty (PTCA): A Report From the PTCA Registry of the National Heart, Lung, and Blood Institute", *American Journal of Cardiology*, 53, 77C–81C, (1984).

Hussain, T., et al., "$^{125}$1–APE Binding to Adenosine Receptors in Coronary Artery: Photoaffinity Labeling With $^{125}$1–azidoAPE", *Journal of Pharmacology and Experimental Therapeutics*, 276(1), 284–288, (Jan. 1996).

Hutchison, A.J., et al., "2–(Arylalkylamino)Adenosine–5'–Uronamides: A New Class of Highly Selective Adenosine $A_2$ Receptor Ligands", *Journal of Medicinal Chemistry*, 33(7), 1919–1924, (1990).

Hutchison, A.J., et al., "CGS 21680C, an $A_2$ Selective Adenosine Receptor Agonist With Preferential Hypotensive Activity", *Journal of Pharmacology and Experimental Therapeutics*, 251(1), 47–55, (1989).

Iannone, M.A., et al., "Effects of Adenosine on Human Neutrophil Function and Cyclic AMP Content", *Topics and Perspectives in Adenosine Research*, eds. E. Gerlach et al., Springer–Verlag, Berlin, Proceedings of the 3rd International Symposium on Adenosine, Munich, Jun. 1986, 286–298, (1986).

Imagawa, D.K., et al., "The Role of Tumor Necrosis Factor in Allograft Rejection", *Transplantation*, 51, 57–62, (Jan. 1991).

Jarvis, M.F., et al., "[$^3$H]CGS 21680, A Selective $A_2$ Adenosine Receptor Agonist Directly Labels A2 Receptors in Rat Brain.", *Journal of Pharmacology and Experimental Therapeutics*, 251(3), 888–893, (Aug. 1989).

Kaminuma, et al., "Effect of T–440, a Novel Type IV Phosphodiesterase Inhibitor, on Allergen–Induced Immediate and Late Asthmatic Reaction and Leukocyte Infiltration into the Airways of Guinea Pigs", *International Archives of Allergy & Immunology*, 112(4), 406–411, (1997).

Kennedy, A.P., et al., "Covalent Modification of Transmembrane Span III of the $A_1$ Adenosine Receptor With an antagonist Photoaffinity Probe.", *Molecular Pharmcology*, 50, 789–798, (Oct. 1996).

Kollias–Baker, C., et al., "Allosteric Enhancer PD 81,723 Acts by Novel Mechanism to Potentiate Cardiac Actions of Adenosine", *Circulation Research,* 75(6), 961–971, (Dec. 1994).

Koshiba, M., et al., "Patterns of $A_{2A}$ Extracellular Adenosine Receptor Expression in Different Functional Subsets of Human Peripheral T Cells. Flow Cytometry Studies With Anti–$A_{2A}$ Receptors Monoclonal Antibodies.", *Molecular Pharmacology,* 55(3), 614–624, (Mar., 1999).

Legrand–Poels, S., et al., "Activation of Human Immunodeficiency Virus Type 1 by Oxidative Stress", *AIDS Research and Human Retroviruses,* 6(12), 1389–1397, (1990).

Lette, J., et al., "Safety of Dipyridamole Testing in 73,806 Patients: The Multicenter Dipyridamole Safety Study", *Journal of Nuclear Cardiology,* 2(1), 3–17, (1995).

Linden, J., "Allosteric Enhancement of Adenosine Receptors", *Purinergic Approaches in Experimental Therapeutics,* Editors: Jacobson, Kenneth A. (Ed) & Jarvis, Michael F (Ed), 85–97, (1997).

Linden, J., "Cloned Adenosine $A_3$ Receptors: Pharmacological Properties, Species Differences and Receptor Functions.", *Trends in Pharmacological Sciences,* 15(8), 298–306, (Aug. 1994).

Linden, J., "Recombinant Techniques as Applied to the Study of $A_1$ Adenosine Receptors", *Adenosine Adenine Nucleotides Molecular Biology Integrative Physiology,* Editors: Belardinelli, Luiz (Ed) & Pelleg, Amir (Ed), 15–19, (1995).

Linden, J., et al., "The Structure and Function of $A_1$ and $A_{2B}$ Adenosine Receptors", *Life Science,* 62(17–18), 1519–1524, (1998).

Luthin, D.R., et al., "Adenosine Receptors", *Biomembranes,* 2B, 321–347, (1996).

Luthin, D.R., et al., "Characterization of Two Affinity States of Adenosine $A_{2a}$ Receptors With a New Radioligand, 2–[2–(4–amino–3–[$^{125}$I]iodophenyl)Ethylamino]Adenosine.", *Molecular Pharmacology,* 47(2), 307–313, (Feb. 1995).

Luthin, D.R., et al., "Comparison of $A_4$ and $A_{2a}$ Binding Sites in Striatum and COS Cells Transfected With Adesosine $A_{2a}$ Receptors.", *Journal of Pharmacology and Experimental Therapeutics,* 272, 511–518, (Feb. 1995).

Luthin, D.R., et al., "Photoaffinity Labeling With 2(–)[2–(4–azido–3(–)[$^{125}$I]–iodophenyl)ethylamino]Adenosine and Autoradiography With 2(–)[2–(4–amino–3(–)[$^{125}$I]iodophenyl)ethylamino]Adenosine of $A_{2a}$ Adenosine Receptor in Rat Brain.", *Journal of Neurochemistry,* 65(5), 2072–2079, (Nov. 1995).

Mannel, D.N., et al., "Tumor Necrosis Factor: A Cytokine Involved in Toxic Effects of Endotoxin", *Reviews of Infectious Diseases,* 9, S602–S606, (1987).

Martin, P.L., et al., "Characterization of 8–(N–methylisopropyl)amino–N$^6$–(5'–andohydroxy–endo-norbornyl)–9–methyladenine (WRC–0571), a Highly Potent and Selective, Non–xanthine Antagonist of $A_1$ Adenosine Receptors.", *Journal of Pharmacology and Experimental Therapeutics,* 276(2), 490–499, (Feb. 1996).

Martin, P.L., et al., "Pharmacology of 2–cyclohexylmethylidenehydrazinoadenosine (WRC–0470), a Novel, Short–acting Adenosine $A_{2A}$ Receptor Agonist That Produces Selective Coronary Vasodilation.", *Drug Development Research,* 40(4), 313–324, (1997).

Matherne, G.P., et al., "Transgenic A1 Adenosine Receptor Overexpression Increases Myocardial Resistence to Ischemia", *Proceedings of the National Academy of Science, USA,* 94, 6541–6546, (Jun., 1997).

Matsuyama, T., et al., "Cytokines and HIV Infection: is AIDS a Tumor Necrosis Factor Disease?", *AIDS,* 5(12), 1405–1417, (1991).

McGarrity, S.T., et al., "Inhibition of Neutrophil Superoxide Anion Generation by Platelet Products: Role of Adenine Nucleotides", *Journal of Leukocyte Biology,* 44(5), 411–421, (1988).

McGarrity, S.T., et al., "Regulation of Human Neutrophil Function by Adenine Nucleotides", *Journal of Immunology,* 142(6), 1986–1994, (1989).

McLaughlin, D.P., et al., "Hemodynamic and Metabolic Correlates of Dipyridamole–induced Myocardial Thallium–201 Perfusion Abnormalities in Multivessel Coronary Artery Disease.", *Amerian Journal of Cardiology,* 73(16), 1159–1164, (Jun., 1994).

Merritt, H.R., et al., "Abnormal Q Waves are Common Early in AMI and Do Not Predict Decreased Myocardial Salvage With Thrombolytic Therapy", *Journal of American College of Cardiology,* 895–897, (Feb. 1994).

Mizumura, T., et al., "PD 81,723, an Allosteric Enhancer of the $A_1$ Adenosine Receptor, Lowers the Threshold for Ischemic Preconditioning in Dogs.", *Circulation Research,* 79(3), 415–423, (Sep. 1996).

Molnar–Kimber, K.L., et al., "Modulation of TNFα and IL–1β From Endotoxin–Stimulated Monocytes by Selective PDE Isozyme Inhibitors", *Agents & Actions,* 39, C77–C79, (1993).

Nabel, E.G., et al., "Site–Specific Gene Expression in Vivo by Direct Gene Transfer into the Arterial Wall", *Science,* 249, 1285–1288, (1990).

Newman, K.D., et al., "Adenovirus–mediated Gene Transfer into Normal Rabbit Arteries Results in Prolonged Vascular Cell Activation, Inflammation and Neointimal Hyperplasia", *Journal of Clinical Investigation,* 96(6), 2955–2965, (1995).

Nielson, C.P., et al., "Effects of Adenosine on Polymorphonuclear Leucocyte Function, Cyclic 3': 5'–adenosine Monophosphate, and Intracellular Calcium", *British Journal of Pharmacology,* 97(3), 882–888, (1989).

Niiya, K., et al., "2–(N'–Alkylidenehydrazino)Adenosines: Potent and Selective Coronary Vasodilators", *Journal of Medicinal Chemistry,* 35(24), 4557–4561, (1992).

Nolte, "Reduction of Postischemic Leukocyte–Endothelium Interaction by Adenosine Via $A_2$ Receptor", *Biological Abstract,* 94(11), Abstract No. 116779, (1992).

O'Regan, M.H., et al., "Adenosine Receptor Agonists Inhibit the Release of γ–Aminobutyric Acid (GABA) From the Ischemic Rat Cerebral Cortex", *Chemical Abstracts,* 117, Abstract No. 104867p, 170, (1992).

Olsson, R.A., et al., "N$^6$ Substituted N–Alkyladenosine–5'–Uronamides: Bifunctional Ligands Having Recognition Groups for A1 and A2 Adenosine Receptors", *Journal of Medicinal Chemistry,* 29(9), 1683–1689, (1986).

Peet, N.P., et al., "Conformationally Restrained, Chiral (Phenylisopropyl)Amino–Substituted Pyrazolo[3,4–d]Pyrimidines and Purines With Selectivity for Adenosine $A_1$ and $A_2$ Receptors", *Journal of Medicinal Chemistry,* 35(17), 3263–3269, (1992).

Pfister, J.R., et al., "Synthesis and Biological Evaluation of the Enantiomers of the Potent and Selective $A_1$– adenosine Antagonist 1,3–dipropyl–8–[2–(5,6–epoxynorbonyl)]–xanthine", *Journal of Medicinal Chemistry*, 40(12), 1773–1778, (Jun., 1997).

Ranhosky, A., et al., "The Safety of Intravenous Dipyridamole Thallium Myocardial Perfusion Imaging", *Circulation*, 81(4), 1205–1209, (Apr., 1990).

Roberts, P.A., et al., "Inhibition by Adenosine of Reactive Oxygen Metabolite Production by Human Polymorphonuclear Leucocytes", *Biochemical Journal*, 227(2), 669–674, (1985).

Robeva, A.S., et al., "Double Tagging Recombitant $A_1$– and $A_{2A}$–Adenosine Receptors With Hexahistidine and the FLAG Epitope. Development of an Efficient Generic Protein Purification Procedure.", *Biochemical Pharmacology*, 51(4), 545–555, (Feb. 1996).

Rosin, D.L., et al., "Immunohistochemical Localization of Adenosine $A_{2A}$ Receptors in the Rat Central Nervous System", *Journal of Comparative. Neurology*, 402(2), 163–186, (Nov. 1998).

Rothe, G.A., et al., "Flow Cytometric Measurement of the Respiratory Burst Activity of Phagocytes Using Dihydrorhodamine 123", *Journal of Immunological Methods*, 138(1), 133–135, (1991).

Sawmiller, D.R., et al., "Effects of Xanthine Amine Congener on Hypoxic Resistence and Venous and Epicardial Adenosine Concentrations.", *Cardiovascular Research*, 28(5), 604–609, (May, 1994).

Schlack, et al., "Adenosine $A_2$–Receptor Activation at Reperfusion reduces Infarct Size and Improves Myocardial Wall Function in Dog Heart", *Biological Abstract*, 96(6), Abstract No. 67801, (1993).

Schrier, D.J., et al., "Effects of Adenosine Agonists on Human Neutrophil Function", *Journal of Immunology*, 137(10), 3284–3289, (1986).

Seekamp, A., et al., "Ischemia—Reperfusion Injury", *Agents and Actions Supplements*, 41, 137–152, (1993).

Sharief, M.K., et al., "Elevated Serum Levels of Tumor Necrosis Factor–α in Guillain–Barre Syndrome", *Annals of Neurology*, 33, 591–596, (Jun. 1993).

Shepherd, R.K., et al., "Adenosine–induced Vasoconstriction in Vivo. Role of the Mast Cell and $A_3$ Adenosine Receptor.", *Circulation Research*, 78(4), 627–634, (Apr., 1996).

Sipka, S., et al., "Adenosine Induced Delay of Expression of AIDS Virus, HIV, in H9T Cells", *Acta. Biochimica et Biophysica Hungarica*, 23(1), 75–82, (1988).

Siragy, H.M., et al., "Sodium Intake Markedly Alters Renal Interstitial Fluid Adenosine", *Hypertension*, 27(3 Pt 1), 404–407, (Mar., 1996).

Smits, P., et al., "Cardiovascular effects of two xanthines and the relation to adenosine antagonism", *Clinical Pharmacology and Therapeutics*, 45(6), 593–599, (1989).

Sullivan, G.W., et al., "Adenosine (ADO) Modulates Endotoxin and TNF–Induced PMN Activation", *Clinical Research*, 41(2), 172A, (1993).

Sullivan, G.W., et al., "Role of $A_{2A}$ Adenosine Receptors in Inflammation", *Drug Development Research*, 45(3/4), 103–112, (1998).

Sullivan, G.W., et al., "The Specific Type IV Phosphodiesterase Inhibitor Rolipram Combined with Adenosine Reduces Tumor Necrosis Factor–α–Primed Neutrophil Oxidative Activity", *International Journal of Immunonopharmacology*, 17(10), 793–803, (1995).

Sullivan, G.W., et al., "Two Methylxanthines, Pentoxifylline (PTX) and Caffeine (CAF) Have Divergent Effects on Tumor Necrosis Factor (TNF)–Primed Human Neutrophil (PMN) Activation", *Clinical Research*, 41(2), 172A, (1993).

Topol, E.J., et al., "Randomised Trial of Coronary Intervention With Antibody Against Platelet IIb/IIIa integrin for Reduction of Clinical Restenosis: Results at Six Months", *The Lencet*, 343(8902), 881–886, (1994).

Tracey, K.J., et al., "Cachectin/Tumor Necrosis Factor Induces Cachexia, Anemia, and Inflammation", *Journal of Experimental Medicine*, 167, 1211–1227, (Mar. 1988).

Tucker, A.L., et al., "$A_1$ Adenosine Receptors. Two Amino Acids are Responsinble for Species Differences in Ligand Recognition", *Journal of Biological Chemistry*, 269(45), 27900–27906, (Nov. 1994).

Ueeda, M., et al., "2–Alkoxyadenosines: Potent and Selective Agonists at the Coronary Artery $A_2$ Adenosine Receptor", *Journal of Medicinal Chemistry*, 34(4), 1334–1339, (1991).

Underwood, D.C., et al., "Inhibition of Antigen–Induced Bronchoconstriction and Eosinophil Infiltration in the Guinea by the Cyclic AMP–Specific Phosphodiesterase Inhibitor, Rolipram", *Chemical Abstracts*, 119(16), Abstract No. 173975, 67, (1993).

Van Calker, D., et al., "Carbamazepine Distinguishes Between Adenosine Receeotors That Mediate Different Second Messenger Responses", *European Journal of Pharmacology*, 206(4), 285–290, (1991).

Walker, B.A., et al., "Adenosine $A_{2a}$ Receptor Activation Delays Apoptosis in Human Neutrophils", *The American Association of Immunologists*, 2926–2931, (1997).

Yoneyama, F., et al., "Vasodepressor Mechanisms of 2–(1–octynyl) –Adenosine (YT–146), a Selective Adenosine $A_2$ Receptor Agonist, Involve the Opening of Glibenclamide–sensitive $K^+$ Channels", *European Journal of Pharmacology*, 213(1), 199–204, (1992).

Ali, H., et al., "Methylxanthines Block Antigen–induced Responses in RBL–2H3 Cells Independently of Adenosine Receptors or Cyclic AMP: Evidence for Inhibition of Antigen Binding to IgE", *Journal of Pharmacology and Experimental Therapeutics*, 258, pp. 954–962, (1991).

Carruthers, A.M., et al., "Hypotensive Responses to the Putative Adenosine $A_3$ Receptor Agonist $N^6$–2–(4–Aminophenyl)–Ethyladenosine in the Rat", *Drug Development Research*, 30, pp. 147–152, (1993).

de Moraes, V.L., et al., "Effect of cyclo–oxygenase inhibitors and modulators of cyclic AMP formation on lipopolysaccharide–induced neutrophil infiltration in mouse lung", *British Journal of Pharmacology*, 117, pp. 1792–1796, (1996).

Fozard, J.R., "Adenosine $A_3$ Receptors Mediate Hypotension in the Angiotensin II–supported Circulation of the Pithed Rat", *British Journal of Pharmacology*, 109 (1), pp. 3–5, (1993).

Hartung, H.P., "Immune–Mediated Demyelination", *Annals of Neurology*, 33 (6), pp. 563–567, (Jun. 1993).

Leclerc, G., et al., "Percutaneous Arterial Gene Transfer in a Rabbit Model", *Journal of Clinical Investigation*, 90 (3), pp. 936–944, (1992).

Bruns, R.F., "Adenosine Receptors—Roles and Pharmacology", *Biological Actions of Extracellular ATP*, 603, Annals of The New York Academy of Sciences, pp. 211–226, (1990).

Bruns, R.F., et al., "Characterization of the $A_2$ Adenosine Receptor Labeled by [$^3$H]NECA in Rat Striatal Membranes", *Molecular Pharmacology*, 29, pp. 331–346, (1986).

Fang, G.D., et al., "A New Selective Adenosine $A_{2a}$ Receptor Agonist, Improves Survival in *E. coli* 026:B6 Lipopolysaccharide (LPS)–Induced Experimental Murine Endotoxemia", *Journal of Investigative Medicine*, Abstract No. 797, p. 148A, (2000).

Heller, L.J., et al., "Effect of Adenosine on Histamine Release and Atrioventricular Conduction During Guinea Pig Cardia Anaphylaxis", *Circulation Research*, 62 (6), pp. 1147–1158, (Jun. 1988).

Ito, B.R., et al., "Role of Cardiac Mast Cells In Complement C5a–induced Myocardial Ischemia", *American Journal of Physiology*, 264 (5), Part 2 of Two Parts, pp. H1346–H1354, (May 1993).

Jolly, S.R., et al., "Effects of Lodoxarnide on Ischemic Reperfused Myocardium", *Journal of Cardiovascular Pharmacology*, 4 (3), pp. 441–448, (1982).

Keller, A.M., et al., "Acute Reoxygeneration Injury in the Isolated Rat Heart: Role of Resident Cardiac Mast Cells", *Circulation Research*, 63 (6), pp. 1044–1052, (Dec. 1988).

Linden, J., et al., "[$^{125}$I] Aminobenzyladenosine, a New Radioligand with Improved Specific Binding to Adenosine Receptors in Heart", *Circulation Research*, 56 (2), pp. 279–284, (Feb. 1985).

Linden, J., et al., "Adenosine Receptors", In: *Handbook of Receptos and Channels—G Protein Coupled Receptors*, Chapter 2, Edited by S.J. Peroutka, Published by CRC Press, Boca Raton, FL, pp. 29–44, (1994).

Linden, J., et al., "Molecular Cloning and Functional Expression of a Sheep $A_3$ Adenosine Receptor with Widespread Tissue Distribution", *Molecular Pharmacology*, 44 (3), pp. 524–532, (Sep. 1993).

Mahan, L.C., et al., "Cloning and Expression of an $A_1$ Adenosine Receptor from Rat Brain", *Molecular Pharmacology*, 40 (1), pp. 1–7, (Jul. 1991).

Mumby, S.M., et al., "G–protein α–subunit expression, myristoylation, and membrane association in COS cells", *Proceedings of the National Academy of Sciences*, 87 (2), pp. 728–732, (Jan. 1990).

Robeva, A.S., et al., "Molecular Characterization of Recombinant Human Adenosine Receptors", *Drug Development Research*, 39, pp. 243–252, (1996).

Schiffmann, S.N., et al., "Distribution of adenosine $A_2$ receptor mRNA in the human brain", *Neuroscience Letters*, 130, pp. 177–181, (1991).

Ukena, D., et al., "Species Differences in Structure–Activity Relationships of Adenosine Agonists and Xanthine Antagonists at Brain $A_1$ Adenosine Receptors", *FEBS Letters*, 209 (1), pp. 122–128, (Dec. 1986).

van Calker, D., et al., "Adenosine Regulates via Two Different Types of Receptors, the Accumulation of Cyclic AMP in Cultured Brain Cells", *Journal of Neurochemistry*, 33, pp. 999–1005, (1979).

Wan, A.A., et al., "Binding of the Adenosine $A_2$ Receptor Ligand ($^3$H)CGS 21680 to Human and Rat Brain: Evidence for Multiple Affinity Sites", *Journal of Neurochemistry*, pp. 1763–1771, (1990).

Wolff, A.A., et al., "Ventricular Arrhythmias Parallel Cardiac Histamine Efflux After Coronary Artery Occlusion in the Dog", *Agents and Actions*, 25 (3/4), pp. 296–306, (1988).*

Abiru et al, J. Med. Chem., vol. 35, pp. 2253–2260, 1992.

Baraldi, P.G., et al., "Synthesis and Biological Activity of a New Series of N6–Arylcarbamoyl, 2–(Ar)arlkynyl–6–0arylcarbamoyl, and N6–Carboxamido derivatives of adenosine–5'–N–ethyluronamide as A1 and A3 Adenosine receptor agonists", *J. Med. Chem.*, vol. 41, No. 17, XP002149470, 3174–3185, (1998).

Mager, P.P., "Neutal network approaches applied to selective A2a adenosine receptor agonists", *Med. Chem. Res.*, vol. 8, No. 6, XP000952528, 277–290, (1998).

Okusa, M.D., et al., "Selective A2A adenosine receptor activation reduces ischemia–reperfusion injury in rat kidney", *Am. J. Physiol.*, vol. 3, Pt 2, XP000952524, F404–F412, (1999).

Koshiba, M., et al., "Patterns of $A_{2A}$ Extracellular Adenosine Receptor Expression in Different Functional Subsets of Human Peripheral T Cells", *The FASEB Journal*, Abstract No. 703.38, p. A944, (1999).

McPherson, J.A., et al., "Effect of Prolonged Adenosine A2A Receptor Activation on Neointimal Formation in the Injured Mouse Carotid Artery", *The FASEB Journal*, Abstract No. 299.2, p. A367, (1999).

\* cited by examiner

| | JMR193 | DWH146e | CGS21680 | ACID DWH146 |
|---|---|---|---|---|
| EC50 | 0.8140 | 0.3164 | 9.214 | 52.92 |

METHODS AND COMPOSITIONS FOR TREATING INFLAMMATORY RESPONSE

CROSS-REFERENCE TO RELATED APPLICATIONS

This application claims priority of U.S. provisional patent applications Ser. Nos. 60/118,029, filed Feb. 1, 1999, and 60/124,316 filed Mar. 12, 1999, 60/133,374, filed May 10, 1999 and 60/135,573, filed May 24, 1999.

The present invention was made with the assistance of U.S. Government funding (NIH Grant ROL HL37942). The U.S. Government has certain rights in this invention.

FIELD OF THE INVENTION

The present invention relates to methods and compositions for preventing tissue injury, i.e., due to inflammatory activity.

BACKGROUND OF THE INVENTION

The inflammatory response serves the purpose of eliminating harmful agents from the body. There is a wide range of pathogenic insults that can initiate an inflammatory response including infection, allergens, autoimmune stimuli, immune response to transplanted tissue, noxious chemicals, and toxins, ischemia/reperfusion, hypoxia, mechanical and thermal trauma. Inflammation normally is a very localized action which serves in expulsion, attenuation by dilution, and isolation of the damaging agent and injured tissue. The body's response becomes an agent of disease when it results in inappropriate injury to host tissues in the process of eliminating the targeted agent, or responding to a traumatic insult.

As examples, inflammation is a component of pathogenesis in several vascular diseases or injuries. Examples include: ischemia/reperfusion injury (N. G. Frangogiannis et al., in *Myocardial Ischemia: Mechanisms, Reperfusion, Protection*, M. Karmazyn, ed., Birkhuser Verlag (1996) at 236–284; H. S. Sharma et al., *Med. of Inflamm.*, 6, 175 (1987)), atherosclerosis (R. Ross, *Nature*, 362, 801 (1993)), inflammatory aortic aneurysms (N. Girardi et al., *Ann. Thor. Surg.*, 64, 251 (1997); D. I. Walker et al., *Brit. J. Surg.*, 59, 609 (1972); R. L. Pennell et al., *J. Vasc. Surg.*, 2, 859 (1985)), and restenosis following balloon angioplasty (see, R. Ross cited above). The cells involved with inflammation include leukocytes (i.e., the immune system cells—neutrophils, eosinophils, lymphocytes, monocytes, basophils, macrophages, dendritic cells, and mast cells), the vascular endothelium, vascular smooth muscle cells, fibroblasts, and myocytes.

The release of inflammatory cytokines such as tumor necrosis factor-alpha (TNFα) by leukocytes is a means by which the immune system combats pathogenic invasions, including infections. TNFα stimulates the expression and activation of adherence factors on leukocytes and endothelial cells, primes neutrophils for an enhanced inflammatory response to secondary stimuli and enhances adherent neutrophil oxidative activity. See, Sharma et al., cited above. In addition, macrophages/dendritic cells act as accessory cells processing antigen for presentation to lymphocytes. The lymphocytes, in turn, become stimulated to act as pro-inflammatory cytotoxic cells.

Generally, cytokines stimulate neutrophils to enhance oxidative (e.g., superoxide and secondary products) and nonoxidative (e.g., myeloperoxidase and other enzymes) inflammatory activity. Inappropriate and over-release of cytokines can produce counterproductive exaggerated pathogenic effects through the release of tissue-damaging oxidative and nonoxidative products (K. G. Tracey et al., *J. Exp. Med.*, 167, 1211 (1988); and D. N. Mannel et al., *Rev. Infect. Dis.*, 9 (suppl. 5), S602–S606 (1987). For example, TNFα can induce neutrophils to adhere to the blood vessel wall and then to migrate through the vessel to the site of injury and release their oxidative and non-oxidative inflammatory products.

Although monocytes collect slowly at inflammatory foci, given favorable conditions, the monocytes develop into long-term resident accessory cells and macrophages. Upon stimulation with an inflammation trigger, monocytes/macrophages also produce and secrete an array of cytokines (including (TNFα), complement, lipids, reactive oxygen species, proteases and growth factors that remodel tissue and regulate surrounding tissue functions.

For example, inflammatory cytokines have been shown to be pathogenic in: arthritis (C. A. Dinarello, *Semin. Immunol.*, 4, 133 (1992)); ischemia (A. Seekamp et al., *Agents-Actions-Supp.*, 41, 137 (1993)); septic shock (D. N. Mannel et al., *Rev. Infect. Dis.*, 9 (suppl. 5), S602–S606 (1987)); asthma N. M. Cembrzynska et al., *Am. Rev. Respir. Dis.*, 147, 291 (1993)); organ transplant rejection (D. K. Imagawa et al., *Transplantation*, 51, 57 (1991); multiple sclerosis (H. P. Hartung, *Ann. Neurol.*, 33, 591 (1993)); AIDS (T. Matsuyama et al., *AIDS*, 5, 1405 (1991); and in alkali-burned eyes (F. Miyamoto et al., *Opthalmic Res.*, 30, 168 (1997)). In addition, superoxide formation in leukocytes has been implicated in promoting replication of the human immunodeficiency virus (HIV) (S. Legrand-Poels et al., *AIDS Res. Hum. Retroviruses*, 6, 1389 (1990)).

It is well known that adenosine and some analogs of adenosine that nonselectively activate adenosine receptor subtypes decrease neutrophil production of inflammatory oxidative products (B. N. Cronstein et al., *Ann. N.Y. Acad. Sci.*, 451, 291 (1985); P. A. Roberts et al., *Biochem. J.*, 227, 669 (1985); D. J. Schrier et al., *J. Immunol.*, 137, 3284 (1986); B. N. Cronstein et al., *Clinical Immunol. and Immunopath.*, 42, 76 (1987); M. A. Iannone et al., in *Topics and Perspective in Adenosine Research*, E. Gerlach et al., eds., Springer-Verlag, Berlin, p. 286 (1987); S. T. McGarrity et al., *J. Leukocyte Biol.*, 44, 411421 (1988); J. De La Harpe et al., *J. Immunol.*, 143, 596 (1989); S. T. McGarrity et al., *J. Immunol.*, 142, 1986 (1989); and C. P. Nielson et al., *Br. J. Pharmacol.*, 97, 882 (1989)). For example, adenosine has been shown to inhibit superoxide release from neutrophils stimulated by chemoattractants such as the synthetic mimic of bacterial peptides, f-met-leu-phe (fMLP), and the complement component $C_5a$ (B. N. Cronstein et al., *J. Immunol.*, 135, 1366 (1985)). Adenosine can decrease the greatly enhanced oxidative burst of PMN (neutrophil) first primed with TNF-α and then stimulated by a second stimulus such as f-met-leu-phe (G. W. Sullivan et al., *Clin. Res.*, 41, 172A (1993)). Additionally, it has been reported that adenosine can decrease the rate of HIV replication in a T-cell line (S. Sipka et al., *Acta. Biochim. Biopys. Hung.*, 23, 75 (1988)). However, there is no evidence that in vivo adenosine has anti-inflammatory activity (G. S. Firestein et al., *Clin. Res.*, 41, 170A (1993); and B. N. Cronstein et al., *Clin. Res.*, 41, 244A (1993)).

It has been suggested that there is more than one subtype of adenosine receptor on neutrophils that can have opposite effects on superoxide release (B. N. Cronstein et al.,*J. Clin. Invest.*, 85, 1150 (1990)). The existence of $A_{2A}$ receptor on neutrophils was originally demonstrated by Van Calker et al. (D. Van Calker et al., *Eur. J. Pharmacology*, 206, 285 (1991)).

There has been progressive development of compounds that are more and more potent and/or selective as agonists of $A_{2A}$ adenosine receptors (AR) based on radioligand binding assays and physiological responses. Initially, compounds with little or no selectivity for $A_{2A}$ receptors were developed, such as adenosine itself or 5'-carboxamides of adenosine, such as 5'-N-ethylcarboxamidoadenosine (NECA) (B. N. Cronstein et al., *J. Immunol.*, 135, 1366 (1985)). Later, it was shown that addition of 2-alkylamino substituents increased potency and selectivity, e.g., CV1808 and CGS21680 (M. F. Jarvis et al., *J. Pharmacol. Exp. Ther.*, 251, 888 (1989)). 2-Alkoxy-substituted adenosine derivatives such as WRC-0090 are even more potent and selective as agonists at the coronary artery $A_{2A}$ receptor (M. Ueeda et al., *J. Med. Chem.*, 34, 1334 (1991)). The 2-alkylhydrazino adenosine derivatives e.g., SHA 211 (also called WRC-0474) have also been evaluated as agonists at the coronary $A_{2A}$ receptor (K. Niiya et al., *J. Med. Chem.*, 35, 4557 (1992)).

There is one report of the combination of relatively nonspecific adenosine analogs, R-phenylisopropyladenosine (R-PIA) and 2-chloroadenosine (Cl-Ado) with a phosphodiesterase (PDE) inhibitor resulting in a lowering of neutrophil oxidative activity (M. A. Iannone et al., *Topics and Perspectives in Adenosine Research*, E. Garlach et al., eds., Springer-Verlag, Berlin, pp. 286–298 (1987)). However, R-PIA and Cl-Ado analogs are actually more potent activators of $A_1$ adenosine receptors than of $A_{2A}$ adenosine receptors and, thus, are likely to cause side effects due to activation of $A_1$ receptors on cardiac muscle and other tissues causing effects such as "heart block."

R. A. Olsson et al. (U.S. Pat. No. 5,278,150) disclose selective adenosine $A_2$ receptor agonists of the formula:

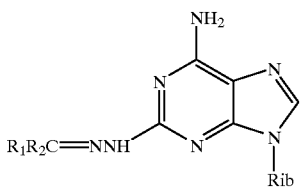

wherein Rib is ribosyl, $R_1$ can be H and $R_2$ can be cycloalkyl. The compounds are disclosed to be useful for treating hypertension, atherosclerosis and as vasodilators.

Olsson et al. (U.S. Pat. No. 5,140,015) disclose certain adenosine $A_2$ receptor agonists of formula:

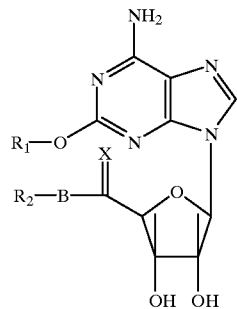

wherein $C(X)BR_2$ can be $CH_2OH$ and $R_1$ can be alkyl- or alkyxyalkyl. The compounds are disclosed to be useful as vasodilators or an antihypertensives.

Linden et al. (U.S. Pat. No. 5,877,180) is based on the discovery that certain inflammatory diseases, such as arthritis and asthma, may be effectively treated by the administration of compounds which are selective agonists of $A_{2A}$ adenosine receptors, preferably in combination with a Type IV phosphodiesterase inhibitor. An embodiment of the Linden et al. invention provides a method for treating inflammatory diseases by administering an effective amount of an $A_{2A}$ adenosine receptor of the following formula:

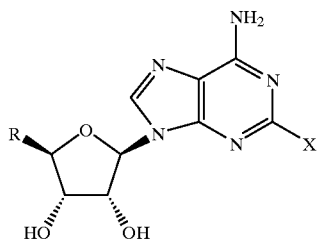

wherein R and X are as described in the patent.

In a preferred embodiment, the Linden et al. invention involves the administration of a Type IV phosphodiesterase (PDE) inhibitor in combination with the $A_{2A}$ adenosine receptor agonist. The Type IV phosphodiesterase (PDE) inhibitor includes racemic and optically active 4-(polyalkoxyphenyl)-2-pyrrolidones of the following formula:

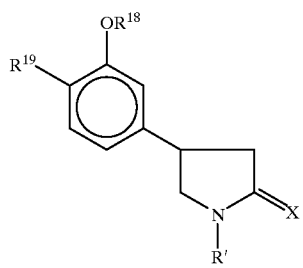

wherein R', $R^{18}$, $R^{19}$ and X are as disclosed and described in U.S. Pat. No. 4,193,926. Rolipram is an example of a suitable Type IV PDE inhibitor included within the above formula.

G. Cristalli (U.S. Pat. No. 5,593,975) discloses 2-arylethynyl, 2-cycloalkylethynyl or 2-hydroxyalkylethynyl derivatives, wherein the riboside residue is substituted by carboxy amino, or substituted carboxy amino ($R_3HNC(O)$—). 2-Alkynylpurine derivatives have been disclosed in Miyasaka et al. (U.S. Pat. No. 4,956,345), wherein the 2-alkynyl group is substituted with $(C_3-C_{16})$alkyl. The '975 compounds are disclosed to be vasodilators and to inhibit platelet aggregation, and thus to be useful as anti-ischemic, anti-atherosclerosis and anti-hypertensive agents.

However, a continuing need exists for selective $A_2$ adenosine receptor agonists useful for therapeutic applications, that have reduced side effects.

SUMMARY OF THE INVENTION

The present invention comprises compounds and methods of their use for the treatment of inflammatory activity in mammalian tissue. The inflammatory tissue activity can be due to pathological agents or can be due to physical, chemical or thermal trauma, or the trauma of medical procedures, such as organ, tissue or cell transplantation, angioplasty (PCTA), inflammation following ischemia/reperfusion, or grafting. The present compounds comprise a novel class of 2-alkynyladenosine derivatives, substituted at the ethyne position by substituted cycloalkyl moieties. Preferably, the riboside residue is substituted at the 5'-position ("X") by an N-alkyl-(or cycloalkyl) carboxyamino ("aminocarbonyl") moiety. Thus, the present invention provides a method for inhibiting the inflammatory response in a mammal, such as a human subject, and protecting the tissue subject to the response, by administering an effective amount of one or more compounds of the invention.

The compounds of the invention have the following general formula (I):

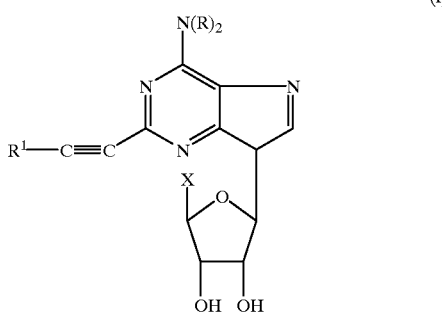

wherein (a) each R is individually hydrogen, $C_1$–$C_6$ alkyl, $C_3$–$C_7$ cycloalkyl, phenyl or phenyl($C_1$–$C_3$)-alkyl;

(b) X is —$CH_2OH$, —$CO_2R^2$, —$OC(O)R^2$, $CH_2OC(O)R^2$ or $C(O)NR^3R^4$;

(c) each of $R^2$, $R^3$ and $R^4$ is individually H, $C_{1-6}$-alkyl; $C_{1-6}$-alkyl substituted with 1–3 $C_{1-6}$-alkoxy, $C_3$–$C_7$ cycloalkyl, $C_{1-6}$-alkylthio, halogen, hydroxy, amino, mono ($C_{1-6}$-alkyl)amino, di($C_{1-6}$-alkyl)amino, or $C_{6-10}$-aryl, wherein aryl may be substituted with 1–3 halogen, $C_{1-6}$-alkyl, hydroxy, amino, mono($C_{1-6}$-alkyl)amino, or di($C_{1-6}$-alkyl)amino; $C_{6-10}$-aryl substituted with 1–3 halogen, hydroxy, amino, mono($C_{1-6}$-alkyl)amino, di($C_{1-6}$-alkyl) amino, or $C_{1-6}$-alkyl;

(d) $R^1$ is (X—(Z)—$_n$[CC$_3$–C$_{10}$)cycloalkyl]-(Z')— wherein Z and Z' are individually ($C_1$–$C_6$)alkyl, optionally interrupted by 1–3 S or nonperoxide O, or is absent, and n is 1–3; or a pharmaceutically acceptable salt thereof.

The invention provides a compound of formula I for use in medical therapy, preferably for use in treating or protecting tissue from inflammation such as an inflammatory response, as well as the use of a compound of formula I for the manufacture of a medicament for the treatment of an inflammatory response due to a pathological condition or symptom in a mammal, such as a human, which is associated with inflammation.

Although certain $A_{2A}$ adenosine receptor agonists have been reported to be vasaodilators, and thus to be useful to directly treat hypertension, thrombus, atherosclerosis and the like, the tissue-protective activity of the compounds of formula (I) is not suggested by the prior art.

The invention also includes the use of a combination of these compounds with type IV phosphodiesterase inhibitors for synergistic decreases in the inflammatory response of immune cells.

The invention also provides a pharmaceutical composition comprising an effective amount of the compound of formula I, or a pharmaceutically acceptable salt thereof, in combination with a pharmaceutically acceptable diluent or carrier, and optionally, in combination with a Type IV phosphodiesterase (PDE) inhibitor. Preferably, the composition is present as a unit dosage form.

Additionally, the invention provides a therapeutic method for preventing or treating a pathological condition or symptom in a mammal, such as a human, wherein the activity of $A_{2A}$ adenosine receptors is implicated and agonism of said activity is desired, comprising administering to a mammal in need of such therapy, an effective amount of a compound of formula I, or a pharmaceutically acceptable salt thereof. It is believed that activation of $A_{2A}$ adenosine receptors inhibits inflammation by effecting neutrophils, mast cells, monocytes/macrophages, T-cells and/or eosinophils. Inhibition of these inflammatory cells results in tissue protection following tissue insults.

Among the inflammatory responses that can be treated (including treated prophylactically) with a compound of formula I, optionally with a Type IV PDE inhibitor, are inflammation due to (a) autoimmune stimulation (autoimmune diseases), such as lupus erythematosus, multiple sclerosis, infertility from endometriosis, type I diabetes mellitus including the destruction of pancreatic islets leading to diabetes and the inflammatory consequences of diabetes, including leg ulcers, Crohn's disease, ulcerative colitis, inflammatory bowel disease, osteoporosis and rheumatoid arthritis;

(b) allergic diseases such as asthma, hay fever, rhinitis, vernal conjunctivitis and other eosinophil-mediated conditions;

(c) skin diseases such as psoriasis, contact dermatitis, eczema, infectious skin ulcers, open wounds, cellulitis;

(d) infectious diseases including sepsis, septic shock, encephalitis, infectious arthritis, endotoxic shock, gram negative shock, Jarisch-Herxheimer reaction, shingles, toxic shock, cerebral malaria, bacterial meningitis, acute respiratory distress syndrome (ARDS), lyme disease, HIV infection, (TNFα-enhanced HIV replication, TNFα inhibition of reverse transcriptase inhibitor activity);

(e) wasting diseases: cachexia secondary to cancer and HIV;

(f) organ, tissue or cell transplantation (e.g., bone marrow, cornea, kidney, lung, liver, heart, skin, pancreatic islets) including transplant rejection, and graft versus host disease;

(g) adverse effects from drug therapy, including adverse effects from amphotericin B treatment, adverse effects from immunosuppressive therapy, e.g., interleukin-2 treatment, adverse effects from OKT3 treatment, adverse effects from GM-CSF treatment, adverse effects of cyclosporine treatment, and adverse effects of aminoglycoside treatment, stomatitis and mucositis due to immunosuppression;

(h) cardiovascular conditions including circulatory diseases induced or exasperated by an inflammatory response, such as ischemia, atherosclerosis, peripheral vascular disease, restenosis following angioplasty, inflammatory aortic aneurysm, vasculitis, stroke, spinal cord injury, congestive heart failure, hemorrhagic shock, ischemia/reperfusion injury, vasospasm following subarachnoid hemorrhage, vasospasm following cerebrovascular accident, pleuritis, pericarditis, and the cardiovascular complications of diabetes;

(i) dialysis, including pericarditis, due to peritoneal dialysis;

(j) gout; and (k) chemical or thermal due to burns, acid, alkali and the like.

Of particular interest and efficacy is the use of the present compounds to treat inflammatory responses due to organ, tissue or cell transplantation, i.e., the transplantation of allogeneic or xenogeneic tissue into a mammalian recipient, autoimmune diseases and inflammatory conditions due to circulatory pathologies and the treatment thereof, including angioplasty, stent placement, shunt placement or grafting. Unexpectedly, it was found that administration of one or more compounds of formula (I) was effective after the onset of the inflammatory response, e.g., after the subject was afflicted with the pathology or trauma that initiates the inflammatory response.

The invention also include a method for measuring the response, or binding a compound of formula I at or to designated $A_{2A}$ adenosine receptor sites comprising said receptors, in vivo or in vitro, with an amount of a compound of formula I effective to bind to said receptors. Tissue or cells comprising ligand bound receptor sites can be used to measure the selectively of test compounds for specific receptor subtypes, the amount of bioactive compound in blood or other physiological fluids, or can be used as a tool to identify potential therapeutic agents for the treatment of diseases or conditions associated with receptor site activation, by contacting said agents with said ligand-receptor complexes, and measuring the extend to displacement of the ligand and/or binding of the agent, or the cellular response to said agent (e.g., cAMP accumulation).

DETAILED DESCRIPTION OF THE INVENTION

Figure 1:
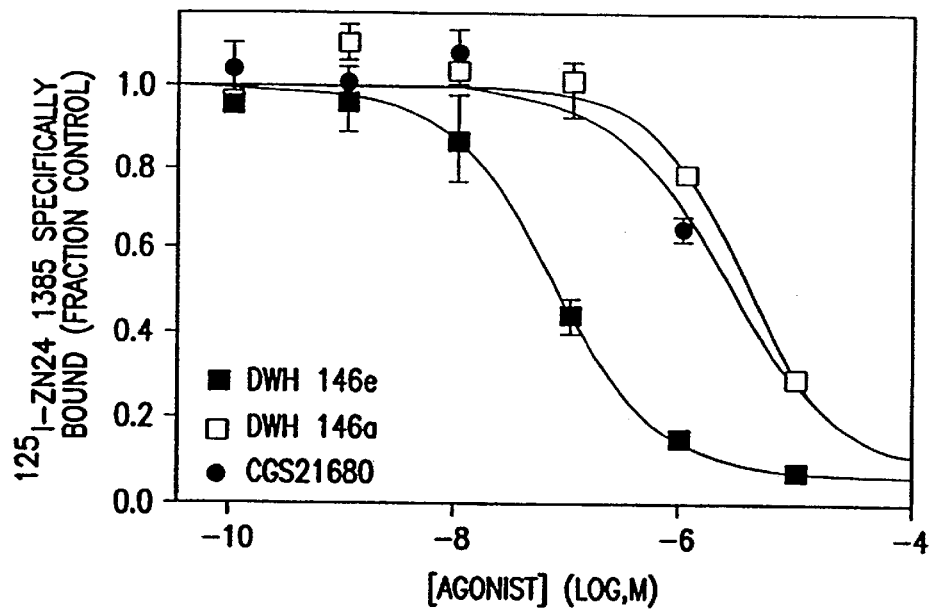
FIG. 1 is a graph depicting the competition by compounds of the invention for binding to recombinant human $A_{2A}$ adenosine receptors.

The following definitions are used, unless otherwise described. Halo is fluoro, chloro, bromo, or iodo. Alkyl, alkoxy, aralkyl, alkylaryl, etc. denote both straight and branched alkyl groups; but reference to an individual radical such as "propyl" embraces only the straight chain radical, a branched chain isomer such as "isopropyl" being specifically referred to. Aryl includes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$ alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that the compounds of formula (I) have more than one chiral center and may be isolated in optically active and racemic forms. Preferably, the riboside moiety of formula (I) is derived from D-ribose, i.e., the 3',4'-hydroxy groups are alpha to the sugar ring and the 2' and 5' groups is beta (3 R, 4 S, 2 R, 5 S). When the two groups on the cyclohexyl group are in the 4-position, they are preferably trans. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, or enzymatic techniques, by synthesis from optically-active starting materials, by chiral synthesis, or by chromatographic separation using a chiral stationary phase) and how to determine adenosine agonist activity using the tests described herein, or using other similar tests which are well known in the art.

Specific and preferred values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl. As used herein, the term "cycloalkyl" compasses bycycloalkyl (norbornyl, 2.2.2-bicyclooctyl, etc.) and tricycloalkyl (adamantyl, etc.), optionally comprising 1–2 N, O or S. Cycloalkyl also encompasses (cycloalkyl)alkyl. Thus, $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl;, 2-cyclopropylethyl, 2-cyclobutylethyl, 2-cyclopentylethyl, or 2-cyclohexylethyl.

$(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$ alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$ alkoxycarbonyl $(CO_2R^2)$ can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanyoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, puridyl (or its N-oxide), thientyl, pyrimidinyl (or its N-oxide), indolyl, isoquinolyl (or its N-oxide) or quinolyl (or its N-oxide).

A specific value for R is amino, monomethylamino or cyclopropylamino.

A specific value for $R^1$ is carboxy- or $(C_1-C_4)$ alkoxycarbonyl-cyclohexyl$(C_1-C_4)$alkyl.

A specific value for $R^2$ is H or $(C_1-C_4)$alkyl, i.e., methyl or ethyl.

A specific value for $R^3$ is H, methyl or phenyl.

A specific value for $R^4$ is H, methyl or phenyl.

A specific value for Z is —$CH_2$— or —$CH_2$—$CH_2$—.

A specific value for X is $CO_2R^2$, $(C_2-C_5)$alkanoylmethyl or amido.

A specific value for n is 1.

Preferred compounds of formula (I) are those wherein each R is H, X is ethylaminocarbonyl and $R^1$ is 4-carboxycyclohexylmethyl (DWH-146a), $R^1$ is 4-methoxycarbonylcyclohexylmethyl (DWH-146e) or $R^1$ is 4-acetoxymethylcyclohexylmethyl (JMR-193). They are depicted below (DWH-146 (acid) and methylester (e)) and JMR-193.

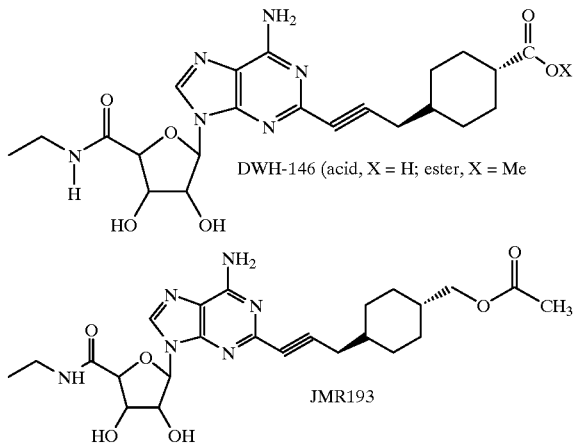

DWH-146 (acid, X = H; ester, X = Me)

JMR193

The synthesis of methyl 4[3-(6-amino-9(5-[(ethylamino)carbonyl]-3,4-dihydroxytetrahydro-Z-furanyl-9 H-2-purinyl)-2-propynyl]-1-cyclohexanecarboxylate (DWH-146e) was accomplished by the cross coupling of an iodo-adenosine derivative (N-ethyl-1'-deoxy-1'-(amino-2-iodo-9 H-purin-9-yl)-β-D-ribofuranuoramide) with methyl 4-(2-propynyl)-1-cyclohexanecarboxylate by utilization of a Pd[11] catalyst. The synthesis of the iodo-adenosine derivative was accomplished from guanosine. Guanosine is first treated with acetic anhydride, which acetalates the sugar hydroxyls, followed by the chlorination of position 6 with tetramethyl ammonium chloride and phosphorousoxychloride. Iodination of position 2 was accomplished via a modified Sandmeyer reaction, followed by displacement of the 6-Cl and sugar acetates with ammonia. The 2' and 3' hydroxyls were protected as the acetonide and the 5' hydroxyl was iodized to the acid with potassium permanganate. Deptrotection of the 2' and 3' acetonide, Fisher esterification of the 5' acid with ethanol and conversion of the resulting ethyl ester to the ethyl amide with ethylamine gave N-ethyl-1'-deoxy-1'-(amino-2-iodo-9 H-purin-9-yl)-β-D-ribofuranuoramide.

The acetylene (methyl 4-(2-propynyl)-1-cyclohexanecarboxylate) was synthesized starting from trans-1,4-cyclohexanedimethanol. Initially the trans-diol was monotosylated followed by displacement of the tosylate with an acetylene anion. The hydroxyl of the resulting hydroxyl acetylene species was oxidized to the acid via Jones reagent followed by methylation with (trimethylsilyl) diazomethane to give methyl 4-(2-propynyl)-1-cyclohexanecarboxylate.

The cross-coupling reaction was performed under the following previously reported conditions. To a solution of N,N-dimethylformamide (0.5 mL), acetonitrile (1mL), triethylamine (0.25 mL), and N-ethyl-1'-deoxy-1'-(amino-2-iodo-9 H-purin-9-yl)-β-D-ribofuranuroamide (25 mg, 0.06 mmol) was added bis(triphenylphosphine)palladium dichloride (1 mg, 2 mol%) and copper(I)iodide (0.06 mg, 0.5 mol%). To the resulting mixture was added methyl 4-(2-propynyl)-1-cyclohexanecarboxylate (54 mg, 0.3 mmol) and the reaction was stirred under $N_2$ atmosphere for 16 hours. The solvent was removed under vacuum and the resulting residue was slash chromatographed in 20% methanol in chloroform ($R_f$=0.45) to give 19 mg (off-white solid, mp 125° C. (decomposed)) methyl of 4[3-(6-amino-9(5-[(ethylamino)carbonyl]-3,4-dihydroxytetrahydro-Z-furanyl)-9 H-2-purinyl)-2-propynyl]-1-cyclohexanecarboxylate (DWH-146e).

DWH-146e and JMR 193 are substantially more potent as inhibitors in inflammatory model systems than the reference compound, CGS21680 (2-[p-(carboxyethyl)-phenylethylamino]5'-N-ethylcarboxamidoadenosine). For example, DWH-146e is about 80 times more potent at $A_{2A}$ receptors and 40 times more selective for $A_{2A}$ over $A_3$ receptors than is CGS21680.

Examples of pharmaceutically acceptable salts are organic acid addition salts formed with acids which form a physiological acceptable anion, for example, tosylate, methanesulfonate, malate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949. Useful dosages of Type IV PDE inhibitors are known to the art. For example, see, U.S. Pat. No. 5,877,180, Col. 12.

Generally, the concentration of the compound(s) of formula (I) in a liquid composition, such as a lotion, will be from about 0.1–25% wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active slat or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 µg/kg, e.g., from about 10 to about 75 µg/kg of body weight per day, such as 3 to about 50 µg per kilogram body weight of the recipient per day, preferably in the range of 6 to 90 µg/kg/day, most preferably in the range of 15 to 60 µg/kg/day.

The compound is conveniently administered in unit dosage form; for example, containing 5 to 1000 µg, conveniently 10 to 750 µg, most conveniently, 50 to 500 µg of active ingredient per unit dosage form.

Ideally, the active ingredient should be administered to achieve peak plasma concentrations of the active compound of from about 0.1 to about 10 nM, preferably, about 0.2 to 10 nM, most preferably, about 0.5 to about 5 nM. This may be achieved, for example, by the intravenous injection of a 0.05 to 5% solution of the active ingredient, optionally in saline, or orally administered as a bolus containing about 1–100 µg of the active ingredient. Desirable blood levels may be maintained by continuous infusion to provide about 0.01–5.0 µg/kg/hr or by intermittent infusions containing about 0.4–15 µg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye. For example, it is desirable to administer the present compositions intravenously over an extended period of time following the insult that gives rise to inflammation.

The ability of a given compound of the invention to act as an $A_{2A}$ adenosine receptor agonist (or antagonist) may be determined using pharmacological models which are well known to the art, or using tests described below.

The invention will be further described by reference to the following detailed examples, which are given for illustration of the invention, and are not intended to be limiting thereof.

EXAMPLE 1

Trans-(1-[4-hydroxymethyl)cyclohexyl]methyl)-4-methylbenzenesulfonate (5.2)

Sodium hydride (1.68 g, 70 mmol) was added to a solution of 10 g (70 mmol) [4-(hydroxymethyl)cyclohexyl] methan-1-ol (5.1) in 700 mL of tetrahydrofuran and stirred for 1 hour p-toluenesulfonyl chloride (13.3 g, 70 mmol) was then added and the reaction mixture was refluxed for 5 hours. The reaction was then cooled to 0° C. and slowly quenched with water until there is no more reactive hydride. Once the hydride was quenched, the reaction mixture was diluted with ether (700 mL) and extracted 2 times with 10% aqueous potassium carbonate (700 mL). The organics were dried using sodium sulfate and the solvent was removed under reduced pressure. The product was purified by chromatography on silica gel column eluting with acetone-dichloromethane (5:95) to give 5.2 (35%). $^1$H NMR (300 MHz, CDCl$_3$) δ 7.75 (d, J=8.3 Hz, 2 H), 7.32 (d, J=8.1 Hz, 2 H), 3.79 (d, J=6.35 Hz, 2 H), 3.39 (d, J=6.35 Hz, 2 H), 2.42 (s, 3 H), 1.75 (m, 4 H), 1.59 (m, 1 H), 1.37 (m, 1 H), 0.9 (m, 4 H). $^{13}$C NMR (300 MHz, CDCl$_3$) δ 145.3, 133.4, 130.3, 130.3, 128.3, 128.3, 75.8, 68.5, 40.6, 37.8, 28.9, 28.9, 28.9, 28.9, 22.1.

EXAMPLE 2

(4-prop-2-ynylcyclohexyl)methan-1-ol (5.3)

Lithium acetylide ethylenediamine complex (90%) (6.4 g, 70 mmol) was added very slowly to a solution of 5.2 (3 g, 10 mmol) in 40 mL of dimethylsulfoxide. The reaction mixture was allowed to stir for 5 days and then slowly quenched at 0° C. with water. This mixture was diluted with ether (300 mL) and extracted 3 times with saturated aqueous ammonium chloride (200 mL). The organics were dried with sodium sulfate. The solvent was removed under reduced pressure and the product was purified by chromatography on silica gel column eluting with ethyl acetate-hexanes (20:80) to give 5.3 (85%). $^1$H NMR (300 MHz, CDCl$_3$) δ 3.41 (d, J=6.5 Hz, 2 H), 2.07 (dd, J=2.5, 6.5 Hz, 2 H), 1.96–1.75 (m, 5 H), 1.41 (m, 2 H), 0.095 (m, 4). $^{13}$C NMR (300 MHz, CDCl$_3$) δ 83.8, 69.6, 68.9, 40.7, 37.7, 32.3, 32.3, 29.6, 29.6, 26.5.

EXAMPLE 3

4-prop-2-ynylcyclohexanecarboxylic acid (5.4)

A solution of chromium trioxide (1.1 g, 11 mmol) in 1.5 M sulfuric acid (40 mL, 27 mmol) was maintained at 0° C. while 5.3 (0.46 g, 3 mmol) in 80 mL of acetone was added over 2 hours. The reaction was then stirred for an additional 2 hours at room temperature. The reaction mixture was diluted with ether (200 mL) and extracted 2 times with water. The organics were dried with sodium sulfate. The solvent was removed under reduced pressure and the product was purified by chromatography on silica gel column eluting with acetone-dichloromethane (70:30) to give 5.4 (75%). $^1$H NMR (300 MHz, CDCl$_3$) δ 2.24 (dt, J=3.66, 12.1 Hz, 1 H), 2.10 (dd, J=2.7, 6.5 Hz, 2 H), 2.04–1.89 (m, 5 H), 1.76 (d, J=2.3 Hz, 1 H), 1.43 (dq, J=3.28, 13.1 Hz, 2 H), 1.03 (dq, J=3.28, 13.1 Hz, 2 H). $^{13}$C NMR (300 MHz, CDCl$_3$) δ 183.2, 83.3, 69.9, 43.4, 36.7, 31.8, 28.9, 26.3.

EXAMPLE 4

Methyl 4-prop-2-ynylcyclohexanecarboxylate (5.5)

(Trimethylsilyl)diazomethane (2.0 M) solution in hexanes (1 mL, 2 mmol) was added to a solution of 5.4 (0.34 g, 2 mmol) in 15 mL of methanol:dichloromethane (3:7). The solvents were removed under reduced pressure resulting in 100% conversion of starting material to produce. $^1$H NMR (300 MHz, CDCl$_3$) δ 2.24 (dt, J=3.66, 12.1 Hz, 1 H), 2.10 (dd, J=2.7, 6.5 Hz, 2 H), 2.06 (dd, J=1.54, 6.54 Hz, 1 H), 2.00–1.89 (m, 3 H), 1.76 (d, J=2.3 Hz, 1 H), 1.43 (dq, J=3.28, 13.1 Hz, 2 H), 1.03 (dq, J=3.28, 13.1 Hz, 2 H). $^{13}$C NMR (300 MHz, CDCl$_3$) δ 176.8, 83.3, 69.8, 51.9, 43.4, 36.7, 31.9, 29.2, 26.3.

EXAMPLE 5

[2 R,3 R,4 R,5 R)-3,4-diacetyloxy-5-(2-amino-6-oxohyropurin-9-yl)oxolan-2-yl]methyl acetate (6.2)

A suspension of 113 g (0.4 mol) of dry guanosine (6.1), acetic anhydride (240 mL, 2.5 mol), dry pyridine (120 mL) and dry DMF (320 mL) was heated for 3.75 hours at 75° C. without allowing the temperature to exceed 80° C. The clear solution was then transferred to a 3L Erlenmyer flask and filled with 2-propanol. Upon cooling the solution to room temperature crystallization was initiated and allowed to proceed at 4° C. overnight. The white solid filtrate was filtered, washed with 2-propanol and recrystallized from 2-propanol to give 6.2 (96%). $^1$H NMR (300 Mhz, CDCl$_3$) δ 8.20 (s, 1H, H-8), 6.17 (d, J=5.41 Hz, 1 H, H-1') 5.75 (t, J=5.39 Hz, 1H, H-2'), 5.56 (t, J=5.0, H-3'), 4.41 (m, 3H, H-4',5'), 2.14 (s, 3H, Ac), 2.11 (s, 3H, Ac), 2.10 (s, 3H, Ac). $^{13}$C NMR (300 MHz, CD$_3$OD) δ 171.10, 170.3, 1702, 157.7, 154.8, 152.4, 136.7, 117.7, 85.5, 80.4, 73.0, 71.3, 64.0, 31.3, 21.2, 21.0.

EXAMPLE 6

[(2R,3R,4R,5R)-3,4-diacetyloxy-5-(2-amino-6-chloropurin-9-yl)oxolan-2-yl]methyl acetate (6.3)

To a 1000 mL flask was added 80 g (0.195 mol) [(2R, 3R,4R,5R)-3-4-diacetyloxy-5-(2-amino-6-oxohyropurin-9- yl)oxolan-2-yl]methyl acetate (6.2), tetramethylammonium chloride (44 g, 0.4 mol), anhydrous acetonitrile (400 mL) and N,N-dimethlaniline (25 mL). The flask was placed in an ice salt bath and cooled to 2° C. To this solution was added dropwise POCl$_3$ (107 mL 1.15 mol) at a rate that maintained the temperature below 5° C. (45 minutes). The flask was then removed from the ice bath, outfitted with a condenser, placed in an oil bath and allowed to reflux for 10 minutes whereas the solution changed to a red/brown color. The solvent was then removed under reduced pressure to yield an oily residue which was transferred to a beaker containing 1000 g of ice and 400 mL of CHCl$_3$ and allowed to stir for 1.5 hours to decompose any remaining POCl$_3$. The organic phase was then removed and the aqueous phase extracted with 3×50 mL of CHCl$_3$ and pooled with the organic phase. The pooled organic was then back extracted with 50 mL of water followed by stirring with 200 mL of saturated NaHCO$_3$. The organic was further extracted with NaHCO$_3$ until the aqueous extract was neutral (2×). The organic was finally extracted with brine and then dried over MgSO$_4$ for 16 hours. To the solution was added 800 mL of 2-propanol after which the solution was concentrated under reduced pressure. To the oily solid was added 200 mL of 2-propanol and the solution was refrigerated overnight. The crystalline product was filtered, washed, and allowed to dry overnight to give 6.3 (77%). $^1$H NMR (300 MHz, CD$_3$OD) δ 8.31 (s, 1H, H-8), 7.00 (s, 2H, NH$_2$) 6.06 (d, J=5.8 Hz, 1H, H-1'), 5.83 (t, J=6.16 Hz, 1H, H-2'), 5.67 (m, 1H, H-3'), 4.29 (m, 3H, H-4',5'), 2.07 (s, 3H, Ac), 1.99 (s, 3H, Ac), 1.98 (s, 3H, Ac). $^{13}$C NMR (300 MHz, CD$_3$OD) δ 171.10, 170.4, 170.2, 160.8, 154.6, 150.8, 142.2, 124.5, 85.8, 80.6, 72.8, 71.2, 63.9, 21.4, 21.3, 21.1.

EXAMPLE 7

[(2R,3R,4R,5R)-3,4-diacetyloxy-5-(6-chloro-2-iodopurin-9-yl)oxolan-2-yl]methyl acetate (6,4)

Isoamyl nitrite (5 mL, 37 mmol) was added to a mixture of 5.12 g (12 mmol) [(2R,3R,4R,5R)-3,4-diacetyloxy-5-(2-amino-6-chloropurin-9-yl)oxolan-2-yl]methyl acetate (6.3), I$_2$ (3.04 g, 12 mmol), CH$_2$I$_2$ (10 mL, 124 mmol), and CuI (2.4 g, 12.6 mmol) in THF (60 mL). The mixture was heated under reflux for 45 minutes and then allowed to cool to room temperature. To this solution was added 100 ml of sat. Na$_2$S$_2$O$_3$ which removed the reddish color due to iodine. The aqueous was extracted 3× with chloroform, which was pooled, dried over MgSO$_4$, and concentrated under reduced pressure. The product was then purified over a silica gel column using CHCl$_3$—MeOH (98:2) to collect [(2R,3R,4R,5R)-3,4-diacetyloxy-5-(6-chloro-2-iodopurin-9-yl)oxolan-2-yl]methyl acetate (6.4) (80% crystallized from EtOH). $^1$H NMR (300 MHz, CDCl$_3$) δ 8.20 (s, 1H H-8), 6.17 (d, J=5.41 Hz, 1H, H-1'), 5.75 (t, J=5.39 Hz, 1H, H-2'), 5.56 (t, J=5.40 Hz, 1H, H-3'), 4.38 (m, 3H, H-4',5'), 2.14 (s, 1H, Ac), 2.11 (s, 1H, Ac), 2.10 (s, 1H, Ac).

EXAMPLE 8

(4R,2R,3R,5R)-2-(6-amino-2-iodopurin-9-yl)-5-(hydroxymethyl)oxolane-3,4-diol (6.5)

To a flask containing 6.0 g (11.1 mmol) [(2R,3R,4R,5R)-3,4-diacetyloxy-5-(6-chloro-2-iodopurin-9-yl)oxolan-2-yl]methyl acetate (6.4) was added 100 ml of liquid NH$_3$ at −78° C. and the solution was allowed to stir for 6 hours. After which time it was allowed to come to r.t. overnight with concurrent evaporation of the NH$_3$ to yield a brown oil. The product was crystallized from hot isopropanol to give 6.5 (80%), m.p. 143–145° C., r.f.=0.6 in 20% MeOH/CHCl$_3$. $^1$H NMR (300 MHz, DMSO-d$_6$) δ 8.24 (s, 1H), 7.68 (s, 2H), 5.75 (d, J=6.16, 1H), 5.42 (d, J=5.40 Hz, 1H), 5.16 (d, J=4.62 Hz, 1H), 4.99 (t, J=5.39 Hz, 1H), 4.67 (d, J=4.81 Hz, 1H), 4.06 (d, J=3.37 Hz, 1H), 3.89 (m, 1H), 3.54 (m, 2H).

EXAMPLE 9

[(1R,2R,4R,5R)-4-(6-amino-2-iodopurin-9-yl)-7,7-dimethyl-3,6,8-trioxabicyclo[3.3.0]oct-2-yl]methan-1-ol (6.6)

To a solution of 2.0 g (5.08 mmol) (4R,2R,3R,5R)-2-(6-amino-2-iodopurin-9-yl)-5-(hydroxymethyl)oxolane-3,4-diol (6.6) in 100 mL acetone was added 9.6 g of p-toluenesulfonic acid and 5 ml of dimethoxypropane. The reaction was stirred at room temperature for 1 hour at which time 15 g of NaHCO$_3$ and then stirred for an additional 3 hours. the residue was filtered and washed 2× with EtOAc. The filtrate was then concentrated under reduced pressure. The residue was chromatographed on a silica gel column with MeOH—CHCl$_3$ (1:99) to give 6.6 (72%) as a solid, m.p. 185–187° C. $^1$H NMR (300 MHz, DMSO-d$_6$) δ 8.22 (s, 1H), H-8), 7.69 (s, 2H), NH$_2$), 6.00 (d, J=2.70 Hz, 1H, H-1'), 5.21 (m, 1H, H-2'), 5.07 (bs, 1H, OH), 4.88 (m, 1H, H-3'), 4.13 (m, 1H, H-4'), 3.47 (m, 2H, H-5'), 1.49 and 1.28 (s, 3H, C(CH$_3$)$_2$).

EXAMPLE 10

(2R,1R,4R,5R)-4-(6-amino-2-iodopurin-9-yl)-7,7-dimethyl-3,6,8-trioxabicyclo[3.3.0]octane-2-carboxylic acid (6.7)

To a stirred solution of 1.6 g (3.7 mmol) of [(1R,2R,4R,5R)-4-(6-amino-2-iodopurin-9-yl)-7,7-dimethyl-3,6,8-trioxabicyclo[3.3.0]oct-2-yl]methan-1-ol (6.6) in 200 mL of H$_2$O was added 0.60 g of KOH and, dropwise, a solution of 1.70 g (10.8 mml) of KMnO$_4$ in 50 mL of H$_2$O. The mixture was set aside in the dark at room temperature for 225 hours. The reaction mixture was then cooled to 5–10° C. and decolorized by a solution of 4 mL of 30% H$_2$O2 in 16 mL of water, while the temperature was maintained under 10° C. using an ice-salt bath. The mixture was filtered through Celite and the filtrate was concentrated under reduced pressure to about 10 mL and then acidified to pH 4 with 2N HCl. The resulting precipitate was filtered off and washed with ether to yield 6.7 (70%) after drying as a white solid, m.p. 187–190° C. $^1$H NMR (300 MHz, DMSO-d$_6$) δ 8.11 (s, 1H, H-8), 7.62 (s, 2H, NH$_2$), 7.46 (s, 1H, COOH), 6.22 (s, 1H, H-1'), 5.42 (d, J=5.71 Hz, 1H, H-2'), 5.34 (d, J=6.16 Hz, 1H, H-3'), 4.63 (s, 1H, H-4'), 1.46 and 1.30 (s, 3H, C(CH$_3$)$_2$).

EXAMPLE 11

(2S,3S,4R,5R)-5-(6-amino-2-iodopurin-9-yl)-3,4-dihydroxyoxolane-2-carboxylic acid (6.8)

A solution of 1.72 g (3.85 mmol) of (2R,1R,4R,5R)-4-(6-amino-2-iodopurin-9-yl)-7,7-dimethyl-3,6,8-trioxabicyclo[3.3.0]octane-2-carboxylic acid (6.7) in 80 mL of 50% HCOOH was stirred at 80° C. for 1.5 hours. The reaction mixture was evaporated under reduced pressure, dissolved in H$_2$O, and the solution was evaporated again. This process was repeated until there was no odor of formic acid in the residue. Recrystallization from water yielded 1.33 g (85%) 6.8 as a white solid, m.p. 221–223° C. dec. $^1$H NMR (300 MHz, DMSO-d$_6$) δ 8.31 (s, 1H, H-8), 7.68 (s, 2H, NH$_2$), 5.90 (d, J=6.55 Hz, 1H, H-1'), 4.42 (m, 1H, H-2'), 4.35 (d, J=2.31 Hz, 1H, H-4'), 4.22 (m, 1H, H-3').

EXAMPLE 12

[(2S,3S,4R,5R)-5-(6-amino-2-iodopurin-9-yl)-3,4-dihydroxyoxolan-2-yl]-N-ethylcarboxamide (6.9)

To a cooled (5° C.) and stirred solution of 1.29 g (3.17 mmol) of (2S,3S,4R,5R)-5-(6-amino-2-iodopurin-9-yl)-3,4-dihydroxyoxolane-2-carboxylic acid (6.8) in 150 mL of absolute ethanol was added dropwise 1.15 mL of ice-cooled $SOCl_2$. The mixture was stirred at room temperature overnight and then brought to pH 8 with saturated aqueous $NaHCO_3$. The mixture was filtered, and then the filtrate was concentrated under reduced pressure to yield a white solid which was dried and then redissolved in 20 mL of dry ethylamine at −20° C. for 3 hours and then at room temperature overnight. The reaction mixture was diluted with absolute ethanol, and the precipitated product was filtered off and washed with dry ether to give 530 mg (72%) of 6.9 as a pure solid, m.p. 232–234° C. $^1$H NMR (300 MHz, DMSO-$d_6$) δ 8.34 (s, 1H, H-8), 8.12 (t, 1H, NH), 7.73 (s, 2H, $NH_2$), 5.85, (d, J=6.93 Hz, 1H, H-1'), 4.54 (m, 1H, H-2'), 4.25 (d, J=1.92 Hz, 1H, H-4'), 4.13 (m, 1H, H-3'), 3.28 (m, 2H, $CH_2CH_3$), 1.00 (t, J=7.2 Hz, 3H, $CH_2CH_3$).

EXAMPLE 13

Methyl-4-(3-{9-[(4S,5S,2R,3R)-5-(N-ethylcarbamoyl)-3,4-dihydroxyoxolan-2-yl]-6-aminopurin-2-yl)}prop-2-ynyl)cyclohexanecarboxylate (DWH-146e)

To a degassed solution of 25 mg (0.063 mmol) of [(2S,3S,4R,5R)-5-(6-amino-2-iodopurin-9-yl)-3,4-dihydroxyoxolan-2-yl]-N-ethylcarboxamide (6.9), 16.9 mg (0.094 mmol) (5.5), and 0.75 mg CuI in 5 mL each of TEA and acetonitrile was added 15 mg of Pd(PPh$_3$)$_4$. The solution was stirred for 24 hours at 70° C. after which time the solution was filtered through celite and chromatographed on silica gel with MeOH—CHCl$_3$ (5:95) to give DWH-146e (24%).

EXAMPLE 14

(4-prop-2-ynylcyclohexyl)methyl acetate (5.6)

Acetic anhydride (0.92 mL, 8.25 mmol) and pyridine (0.2 mL, 2.5 mmol) were added to a solution of 5.3 (250 mg, 1.65 mmol) in 25 mL ether. The reaction was allowed to stir at ambient temperature for 24 hours. Water was added to the reaction and the organic was further extracted with 10% $NaHCO_3$. The organic layer was dried with $MgSO_4$ and evaporated. The residue was chromatographed on silica gel with EtOAc-Hexanes (5:95) to yield 5.6 (47%).

EXAMPLE 15

[4-(3-{9-(4S,5S,2R,3R)-5-(N-ethylcarbamoyl)-3,4-dihydroxyoxolan-2-yl]-6-aminopurin-2-yl}prop-2-ynyl)cyclohexyl]methyl acetate (JMR193)

To a degassed solution of 125 mg (0.29 mmol) of [(2S,3S,4R,5R)-5-(6-amino-2-iodopurin-9-yl)-3,4-dihydroxyoxolan-2-yl]-N-ethylcarboxamide (6.9), 150 mg (0.77 mmol) (5.6), and 1.0 mg CuI in 1.3 mL of TEA and 4 mL DMF was added to 25 mg of Pd(PPh$_3$)$_4$. The solution was stirred for 72 hours at 60° C. after which time the solution was filtered through celite and chromatographed on silica gel with MeOH—CHCl$_3$ (5:95) to give JMR193 (10%).

EXAMPLE 16

Radioligand Binding Studies

Binding to $A_{2A}$ receptors was evaluated with the radioligand $^{125}$I-ZM241385. FIG. 1 depicts the competition by selective agonists for binding to recombinant human $A_{2A}$ adenosine receptors. DWH-146e is highly selective for the recombinant human $A_{2A}$ (hA2A) subtype. Selectivity for the $A_3$ receptor (not shown) is less impressive, but still about 50-fold. DWH-146e is about 5 and 50 times more potent than WRC0470 and CGS21680, respectively (FIG. 1). An unexpected and interesting finding is that the ester, DWH-146e also is about 50 times more potent than the acid, DWH-146a (FIG. 1).

EXAMPLE 17

Effect of DWH-146e and JMR193 on Neutrophil Oxidative Activity

A. Materials f-met-leu-phe (fMLP), luminol, superoxide dismutase, cytochrome C, fibrinogen, adenosine deaminase, and trypan blue were obtained from Sigma Chemical. Ficoll-hypaque was purchased from ICN (Aurora, Ohio), and Cardinal Scientific (Sante Fe, N.M.) and Accurate Chemicals and Scientific (Westerbury, N.Y.), endotoxin (lipopolysaccharide; E. coli K235) was from List Biologicals (Campbell, Calif.). Hanks balanced salt solution (HBSS), and limulus amebocyte lysate assay kit were from BioWittaker (Walkersville, Md.). Human serum albumin (HSA) was from Cutter Biological Elkhart, Ind.). Recombinant human tumor necrosis factor-alpha was supplied by Dianippon Pharmaceutical Co. Ltd. (Osaka, Japan). ZM241385 (4-(2-[7-amino-2-(2-furyl)-[1,2,4]-triazolo[2,3-a][1,3,5]triazin-5-yl amino]ethyl)phenol) was a gift from Simon Poucher, Zeneca Pharmaceuticals, Cheshire, UK. Stock solutions (1 mM and 10 mM in DMSO) were made and stored at −20° C.

B. Human neutrophil preparation

Purified neutrophils (~98% neutrophils and >95% viable by trypan blue exclusion) containing <1 platelet per 5 neutrophils and <50 pg/ml endotoxin (limulus amebocyte lysate assay) were obtained from normal heparinized (10 U/ml) venous blood by a one step Ficoll-hypaque separatin procedure (A. Ferrante et al., *J. Immunol. Meth.*, 36, 109 (1980)).

C. Release of inflammatory reactive oxygen species from primed and stimulated human neutrophils Chemiluminescence Luminol-enhanced chemiluminescence, a measure of neutrophil oxidative activity, is dependent upon both superoxide production and mobilization of the lysosomal granule enzyme myeloperoxidase. The light is emitted from unstable high-energy oxygen species generated by activated neutrophils. Purified neutrophils (5–10×10$^5$/ml) were incubated in Hanks balanced salt solution containing 0.1% human serum albumin (1 ml) with or without DWH-146a, DWH-146e, CGS21680, of JMR193 with or without rolipram and with or without tumor necrosis factor-alpha (1 U/ml) for 30 minutes at 37° C. in a shaking water bath. Then luminol (1×10$^{-4}$ M) enhanced f-met-leu-phe (1 mcM) stimulated chemiluminescence was read with a Chronolog® Photometer (Crono-log Corp., Havertown, Pa.) at 37° C. for 2–4 minutes. Chemiluminescence is reported as relative peak light emitted (=height of the curve) compared to samples with tumor necrosis factor-alpha and without DWH, JMR or rolipram.

D. Results

Figure 2:
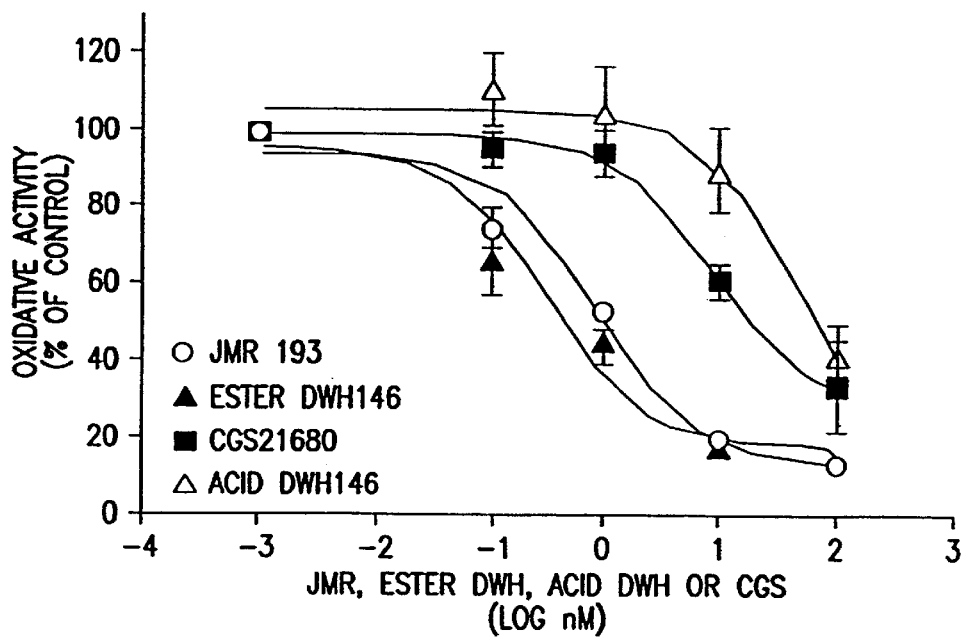
FIG. 2 is a graph depicting the decrease in human neutrophil oxidative activity by compounds of the invention.

As shown in FIG. 2, JMR193 and DWH-146e both decreased tumor necrosis factor-alpha-primed f-met-leu-phe-stimulated human neutrophil oxidative activity as measured by luminol-enhanced chemiluminescence more effectively than the adenosine $A_{2A}$ receptor agonist CGS21680. The horizontal axis gives the concentration of CGS21680, DWH-146a, DWH-146e or JMR193 (log nM). The vertical axis gives the resulting peak human neutrophil activity as relative amount of stimulated release of reactive oxygen species as measured with luminol-enhanced chemiluminescence compared to control samples which were not primed with tumor necrosis factor-alpha. Means SEM (n=4–5 separate experiments).

The data below the horizontal axis in FIG. 2 gives the $EC_{50}$ for reducing the human neutrophil activity (based on the data in FIG. 2). Means SEM (n=4–5 separate experiments). *$p<0.05$ decreased $IC_{50}$ compared to CGS21680.

JMR193 and DWH-146e decreased the stimulated-neutrophil oxidative burst with $EC_{50}$'s less than 1 nM (0.8 and 0.3 nM, respectively). In contrast, the free acid $A_{2A}$ adenosine receptor agonists DWH-146a and CGS21680 were not as effective in inhibiting the oxidative burst (53 and 9 nM, respectively; FIG. 2). DWH-146e inhibition of the stimulated neutrophil oxidative burst was antagonized by the selective $A_{2A}$ AR antagonist ZM241385.

Figure 3:
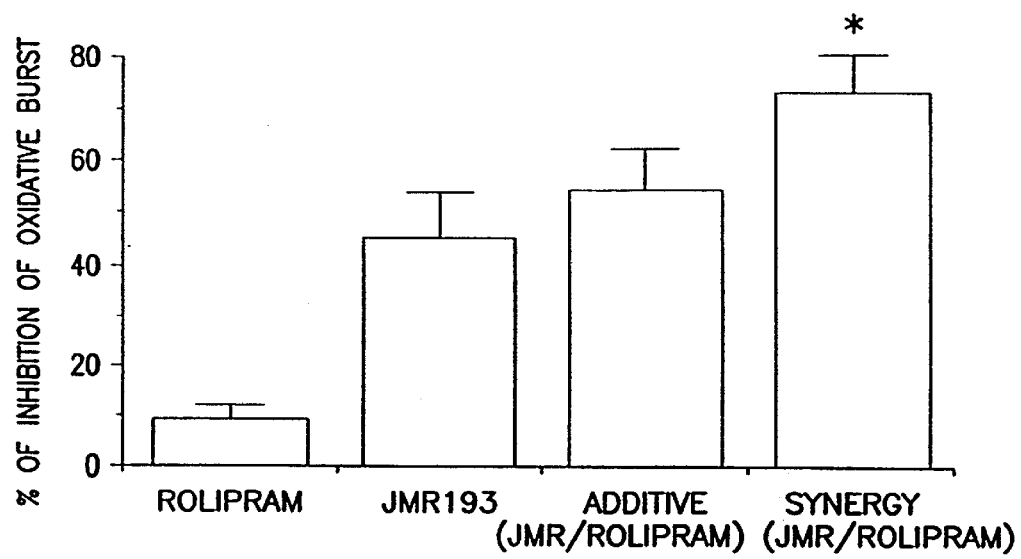
FIG. 3 is a graph depicting the inhibition of human neutrophil oxidative activity by a compound of the invention (JMR193) with and without rolipram.

As shown in FIG. 3, JMR193 (1 nM) with rolipram (100 nM) synergistically decreased stimulated release of reactive oxygen species. Human neutrophils were primed with tumor necrosis factor-alpha (1 U/ml) and stimulated with f-met-leu-phe (1 $\mu$M). The vertical axis gives the percent inhibition of oxidative activity as measured by luminol-enhanced chemiluminescence. Means SEM (n=4 separate experiments. *$p<0.05$ synergy between JMR193 and rolipram compared to additive activity.

Figure 4:
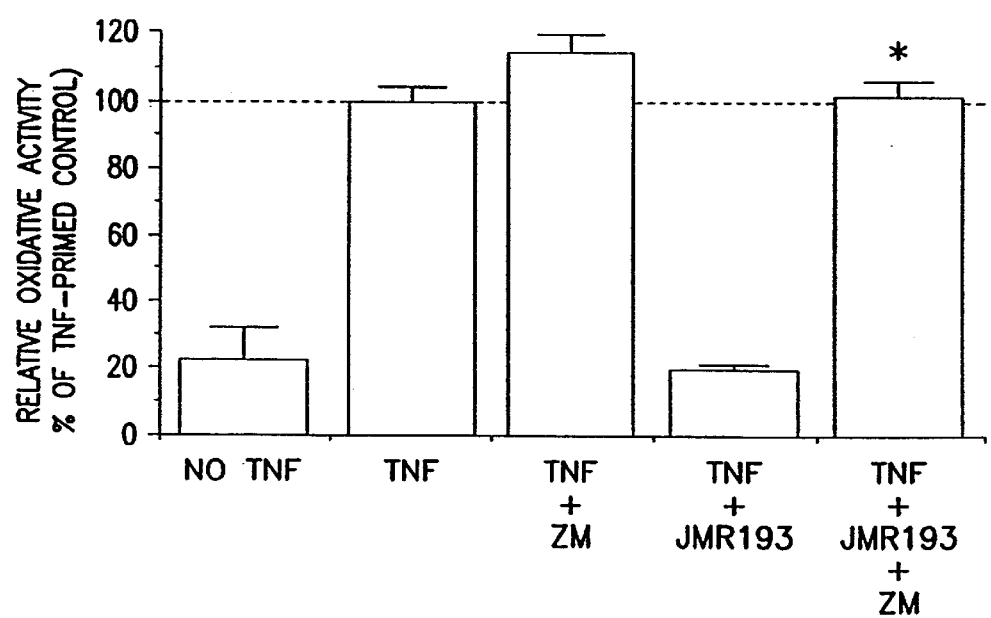
FIG. 4 is a graph depicting the ability of ZM241385 to counteract JMR193 inhibited neutrophil oxidative activity.

As shown in FIG. 4, the highly selective $A_{2A}$ adenosine receptor antagonist ZM241385 (100 nM) (ZM) counteracted human neutrophil oxidative activity inhibited by JMR193 (10 nM) as measured by luminol-enhanced chemiluminescence. Means SEM of 4 separate experiments. *$p=0.0004$ ZM241385 counteracted JMR193 inhibited oxidative activity.

E. Human neutrophil $[cAMP]_i$ and neutrophil adherence to a biological surface

A 24 well tissue culture plate was coated with human fibrinogen (5 mg/ml in 1.5% sodium bicarbonate; 0.5 ml/well; Sigma Chemical) overnight at 37° C. in 5% $CO_2$. Neutrophils (3–4×10$^6$/0.5 ml/sample) were incubated within a well of the coated plate for 45 minutes in 0.5 ml of HBSS containing 0.1% HSA and ADA (1 U/ml) in the presence and absence of recombinant human TNFα (10 U/ml), DWH-146e (3–300 nm), rolipram (300 nM), and/or ZM241385 (100 nM). Following incubation, 0.5 ml HCl (0.2 N) was added to the wells and incubated for 45 minutes more at room temperature to extract the cAMP. The samples were then centrifuged in a microfuge for 2 minutes to remove cell debris. Half ml samples were frozen for cAMP analyses (B. Brooker et al., Science, 194, 270 (1976)). The wells were washed twice with normal saline and the remaining monolayer digested with 0.2 ml of 0.2 N NaOH containing SDS for 2 hours at room temperature. The protein samples were then frozen (–70° C.) for later protein analysis to determine relative PMN adherence (K. P. Stowell et al., Anal. Biochem., 85, 572 (1978)).

Results

Figure 5:
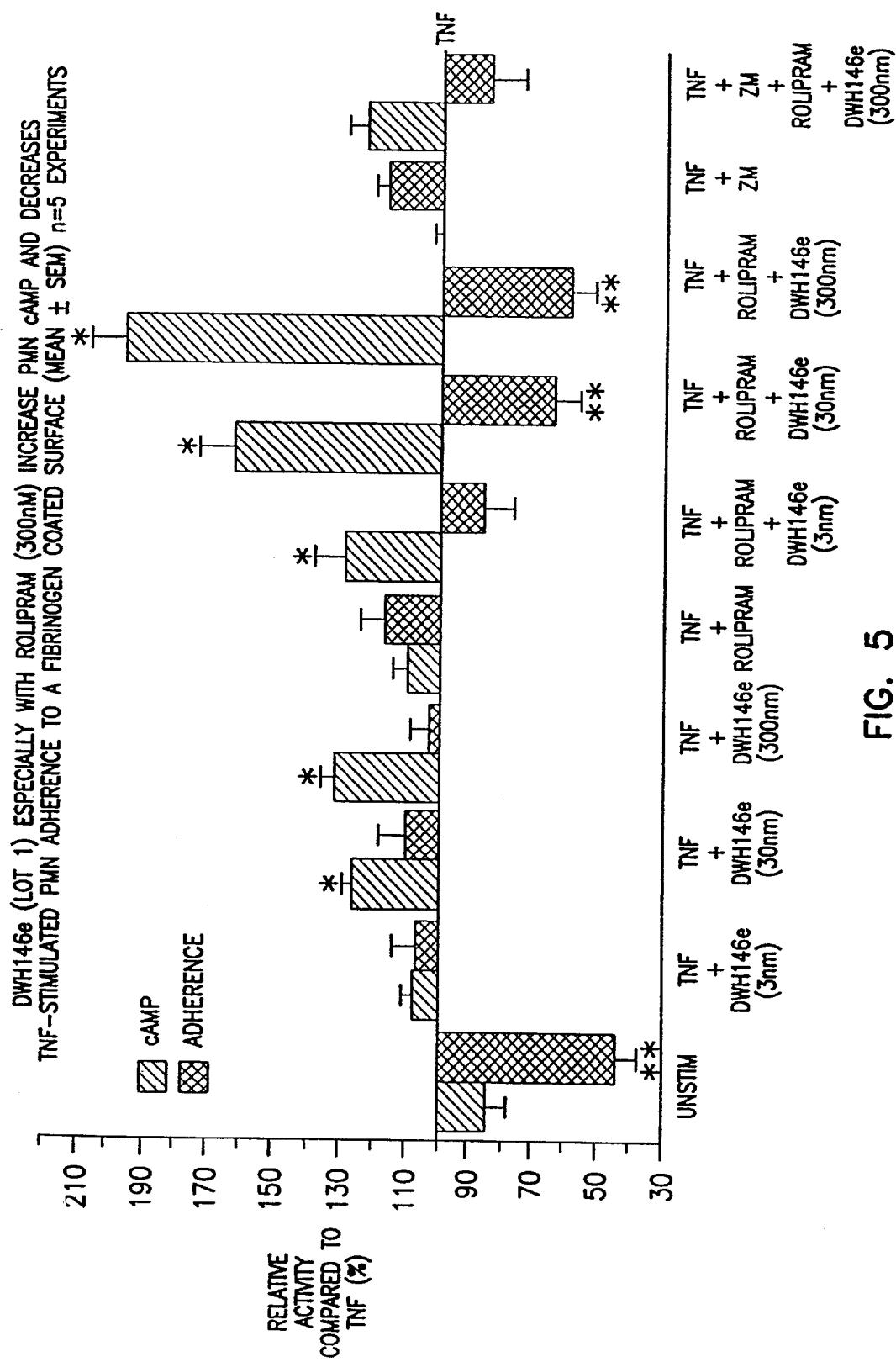
FIG. 5 is a graph depicting the effect of a compound of the invention on neutrophil cAMP content and adherence to a biological surface.

DWH-146e (30–300 nM) alone and synergistically with rolipram (300 nM) increased human neutrophil cAMP content and with rolipram synergistically decreased neutrophil adherence to a fibrinogen-coated surface (FIG. 5). The effects of DWH-146e (300 nM)+rolipram (300 nM) on neutrophil cAMP production and adherence were counteracted by the selective $A_{2A}$ adenosine receptor antagonist, ZM241385 (ZM; 100 nM). Mean SEM of 5 separate experiments. *$p<0.05$ increased neutrophil [cAMP] compared to without DWH-146e; **$p<0.05$ decreased neutrophil adherence compared to no DWH-146e.

F. Adherent human neutrophil oxidative activity

Methods. Using methods modified from Section E, neutrophils (2×10$^6$/ml) from Ficoll-Hypaque separation were incubated 15 minutes 37° C. in 0.45 ml of Hanks balanced salt solution containing 0.1% human serum albumin and adenosine deaminase (1 U/ml), rolipram (300 nM), and DWH-146e (3–300 nM). Following incubation, cytochrome C (120 $\mu$M) and catalase (0.062 mg/ml) are added in the presence and absence of recombinant human tumor necrosis factor-alpha (1 U/ml) and 200 $\mu$l aliquots of cell suspension were immediately transferred to duplicate wells of a 96 well flat-bottomed tissue culture plate which had been coated overnight with human fibrinogen. The optical density of the samples were read at 550 nm against matched superoxide dismutase (200 U/ml) samples.

G. Results

Figure 6:
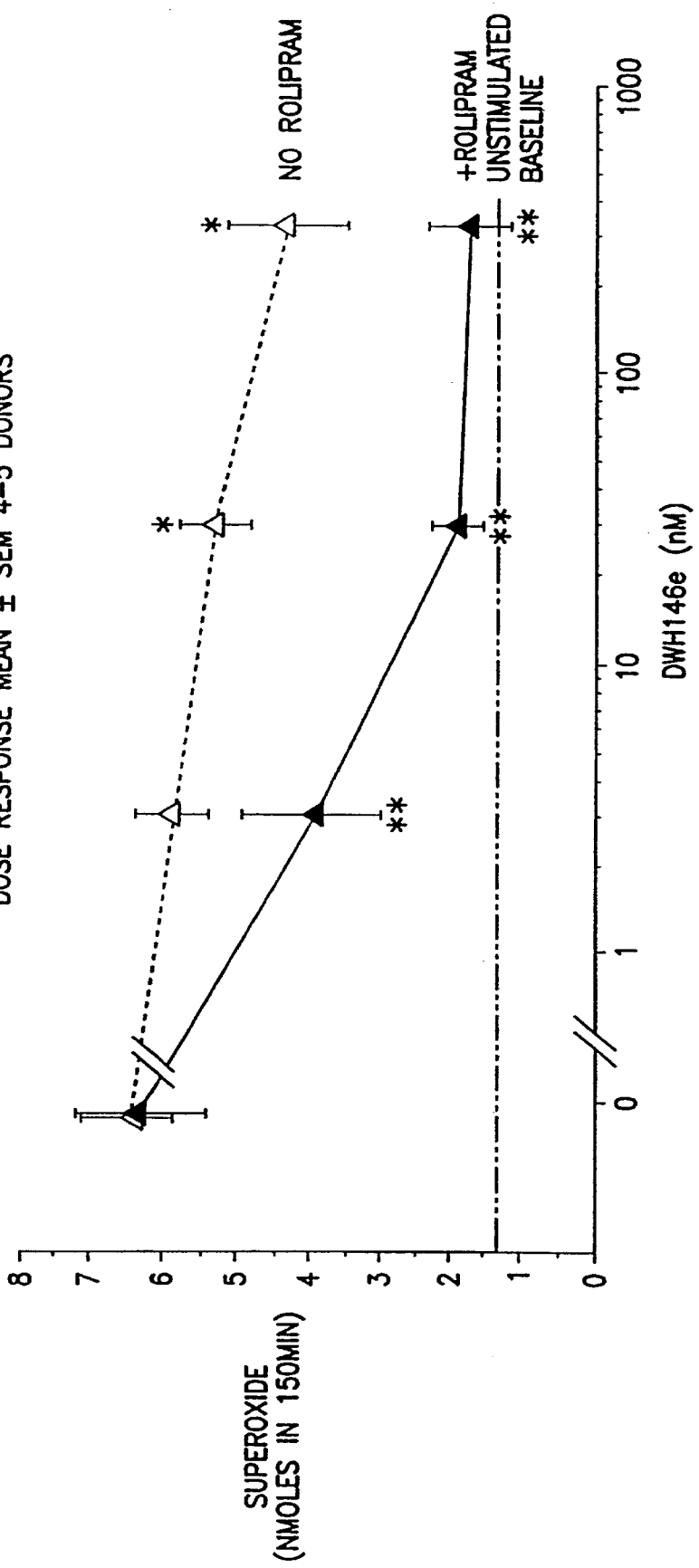
FIG. 6 is a graph depicting the ability of compound DWH-146e to inhibit PMN superoxide release on a biological surface.

As shown in FIG. 6, inhibition of tumor necrosis factor-alpha (TNF)-stimulated adherent human neutrophil superoxide release on a fibrinogen-coated surface was accomplished by rolipram (300 nM) and DWH-146e. DWH-146e decreased the oxidative burst of adhering neutrophils, and synergistically decreased the oxidative burst in the presence of rolipram, which by itself did not affect neutrophil oxidative activity. The horizontal axis give the DWH-146e concentration in nM and the vertical axis gives the amount of superoxide released by the neutrophils as measured by cytochrome c reduction. There was marked synergy with DWH-146e and the type IV PDE inhibitor, rolipram, to decrease tumor necrosis factor-alpha-stimulated adherent human neutrophil oxidative activity. Means SEM of replicates from 4–5 separate experiments. *$p<0.05$ decreased superoxide release compared to without DWH-146e; **$p<0.05$ decreased superoxide release compared to with rolipram and without DWH-146e.

EXAMPLE 18

Treatment of Ischemia/Reperfusion (I/R) Injury in Kidney with DWH-146e

Figure 7:
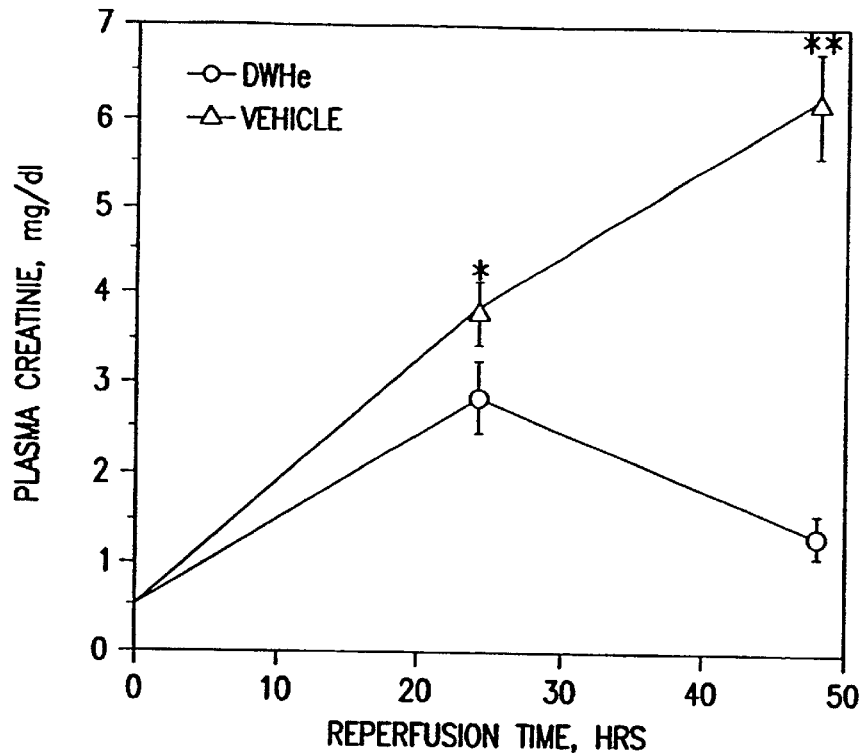
FIG. 7 is a graph depicting the ability of compound DWH-146e to reduce plasma creatinine following ischemia/reperfusion injury in rats.

To determine whether or not DWH-146e induced $A_{2A}$ adenosine receptor activation reduces plasma creatinine at 24 and 48 hours following I/R injury in rats, rat kidneys were subjected to 45 minutes ischemia and 24 or 48 hours of reperfusion. DWH-146e (0.004 $\mu$g/kg/min) or vehicle was administered continuously via minipump beginning 5 hours prior to I/R. As shown in FIG. 7, DWH-146e significantly decreased plasma creatinine in 7/7 rats (P<0.05) and in 6/6 rats treated with DWH-146e (P<0.001), at 24 and 48 hours, respectively.

Figure 8:
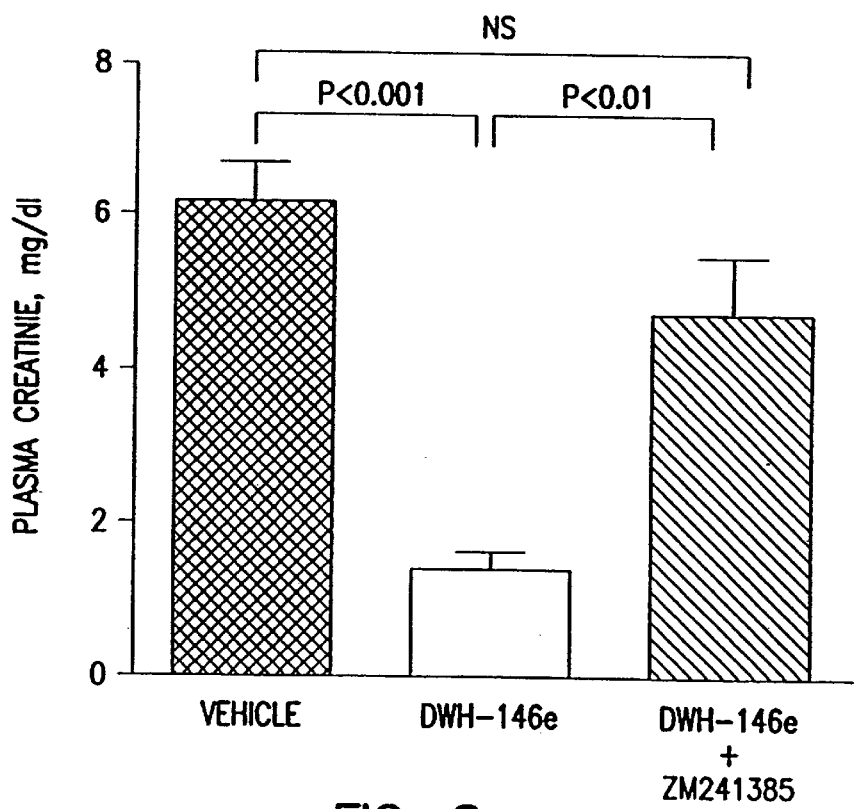
FIG. 8 is a graph depicting the effect of compound ZM241385 on renal function that had been improved following I/R injury by DWH-146e.

To determine whether or not the effect of DWH-146e on reduction of plasma creatinine in rats subjected to I/R is $A_{2A}$-receptor mediated, rat kidneys were subjected to 45 minutes ischemia followed by 48 hours reperfusion. DWH-146e (0.004 $\mu$g/kg/min) was administered continuously via minipump beginning 5 hours prior ischemia. As shown in FIG. 8, the improvement in renal function was reversed by the $A_{2A}$ antagonist ZM-241385 (0.003 $\mu$g/kg/min-equimolar delivery rate compared with DWH-146e) (*P<0.001 for Vehicle vs. DWH; **P<0.05 DWH vs. DWH/ZM. N=5 for Vehicle, DW; N=6 for DWH/ZM. ANOVA followed by Bonferroni correction).

DWH-146e, at concentrations that have no hemodynamic effects, prevents renal edema, necrosis and red cell pooling in the inner medulla.

The protection against renal damage afforded by DWH-146e (0.01 μg/kg/min s.c. for 48 hours) was correlated with a dramatic inhibition of neutrophil adherence to vascular endothelium. It is believed that inhibition by DWH-146e of the interaction between neutrophils and vascular endothelium is responsible, at least in part, for the protection against renal damage.

Figure 9:
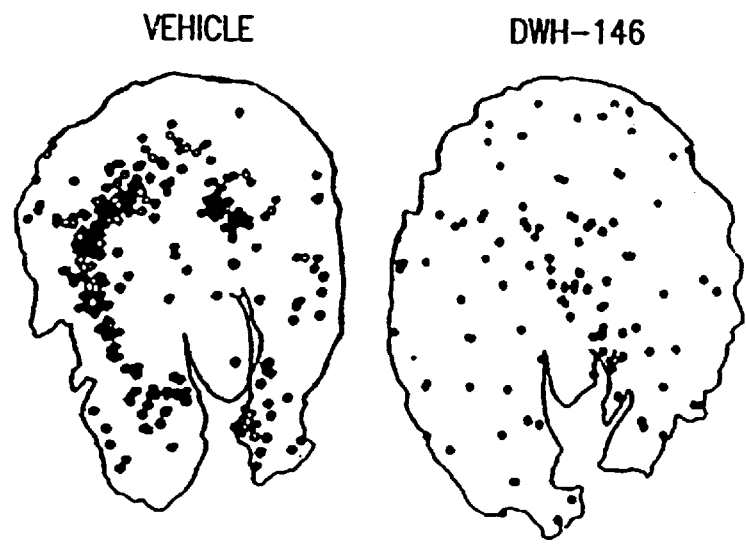
FIG. 9 is a comparative image of treated and untreated section of rat kidney subjected to I/R injury.

To determine whether or not $A_{2A}$-AR activation reduces neutrophils in the outer medulla of rats subjected to I/R, using Neurolucida®, the kidney was viewed under 100×mag and the entire kidney was drawn. PMNs were counted by viewing kidney sections under 250×mag. Kidney sections were overlaid with optical frames viewed under the microscope and all PMNs were counted within each frame. This system prevents counting of PMNs more than once. As shown in FIG. 9, the density of neutrophils was $15.65/mm^2$ for vehicle and $3.02/mm^2$ DWH-146e treatment.

EXAMPLE 19

Effect of DWH-146e on Lung Reperfusion Injury

A. Methods

An isolated, whole blood-perfused, ventilated rabbit lung model was used. Donor rabbits underwent lung harvest after pulmonary arterial $PGE_1$ injection and Euro-Collins preservation solution flush, and lungs were preserved for 18 hours at 4° C. Group I lungs (n=9) served as control subjects. Group II lungs (n=9) were reperfused with whole blood that was first passed through a leukocyte-depleting filter. In group III (n=9), DWH-146e was added to the blood reperfusate (25 μg/kg) immediately before reperfusion and was administered throughout the reperfusion period (1 μg/kg/min). All lungs were reperfused for 30 minutes, and pulmonary artery pressure (PAP), pulmonary vascular resistance (PVR), airway compliance (CPL) and arterial oxygenation were recorded. Mycloperoxidase activity (MPO) was recorded to quantify neutrophil sequestration, and wet/dry weight ratios were measured to demonstrate pulmonary edema.

B. Results

Figure 10:
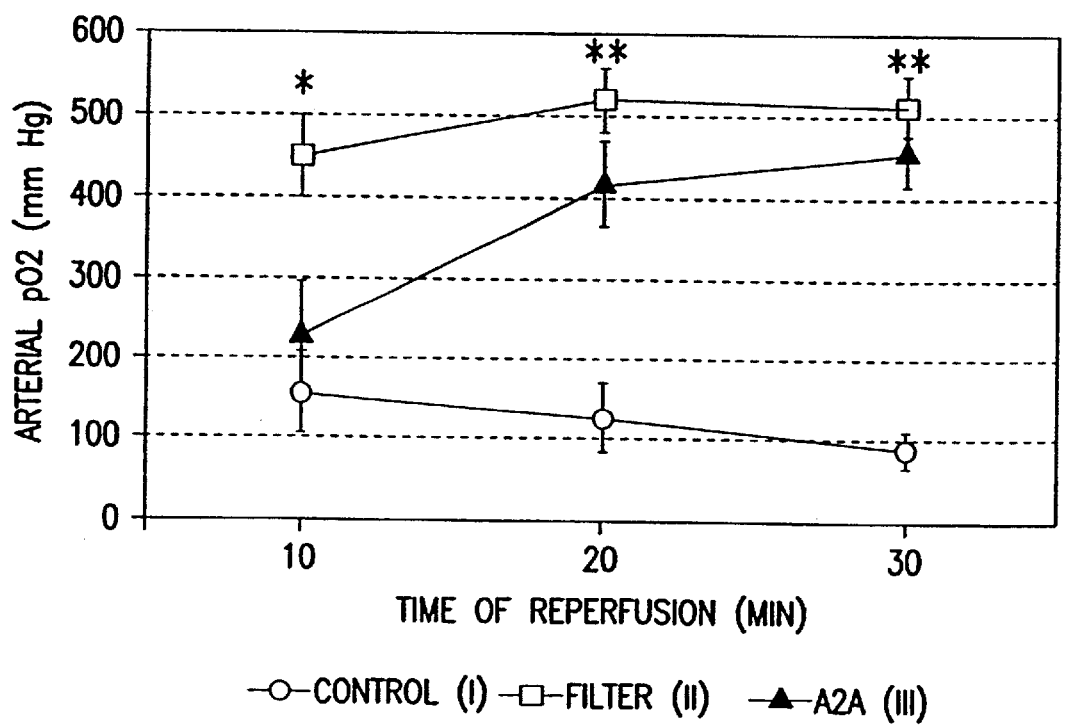
FIG. 10 is a graph depicting the effect of DWH-146e on arterial $pO_2$ following lung reperfusion injury in rabbits.

Arterial oxygenation in group II and group III was significantly higher than that of group I after 30 minutes of reperfusion (514.27±35.80 and 461.12±43.77 vs. 91.41±20.58 mm Hg, p<0.001. As shown in FIG. 10, group III lungs displayed a progressive involvement in $pO_2$ throughout reperfusion. Leukocyte depletion in group II lungs improved arterial oxygenation in early reperfusion. *p=0.004 (group II versus groups I and III); **p<0.0001 (groups II and III versus group I).

Figure 11:
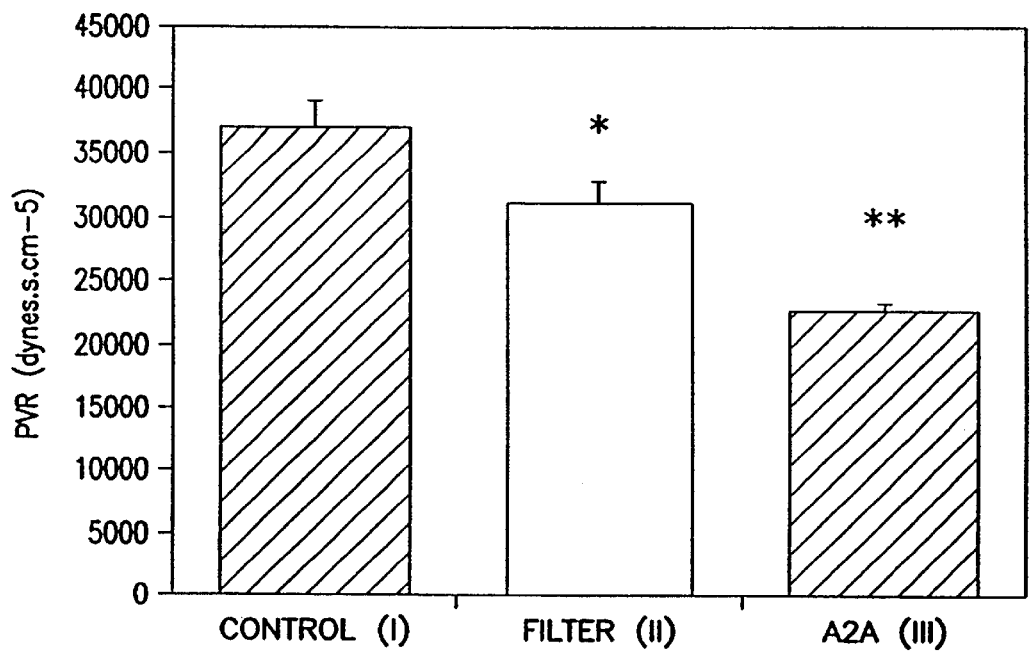
FIG. 11 is a graph depicting the effect of DWH-146e on pulmonary muscular resistance following lung reperfusion injury.
Figure 12:
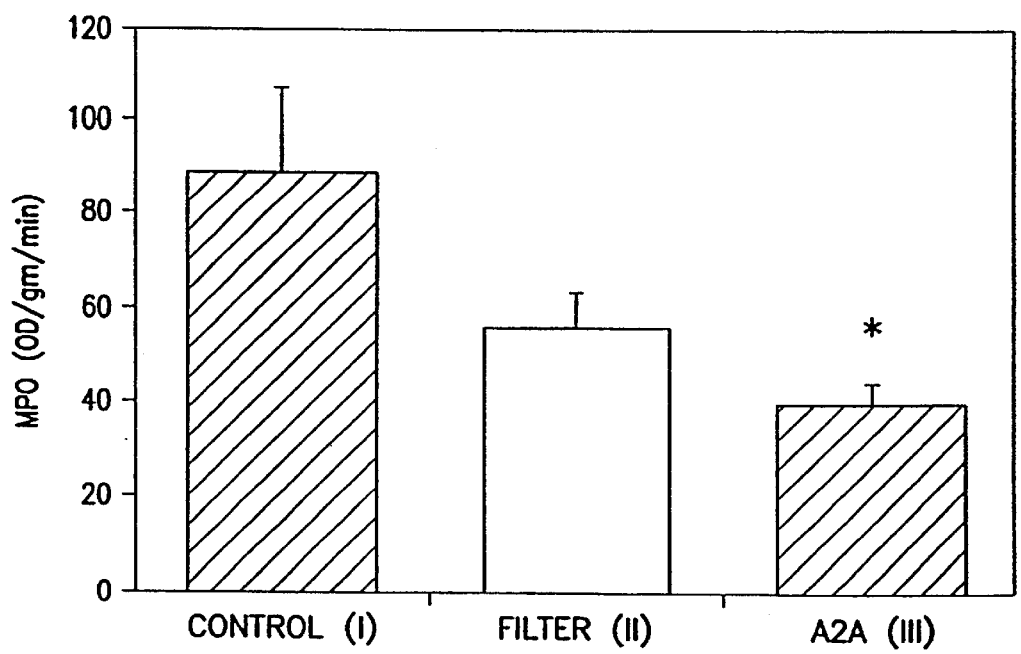
FIG. 12 is a graph depicting the effect of DWH-146e on myeloperoxidase activity following lung reperfusion injury.

As shown in FIG. 11, mean PVR in group II was significantly reduced when compared to controlled lungs (*p<0.001). PVR of group III lungs was significantly lower than even those lungs that underwent reperfusion with leukocyte-depleted blood (**p<0.001 versus groups I and II). Pulmonary vascular resistance was significantly reduced in group III (22,783±357 dynes·s·cm$^{-5}$) compared to both group II and group I (31,057±1743 and 36,911±2173 dynes·s·cm$^{-5}$, p<0.001). Airway compliance was improved in groups II and III when compared to group I (1.68±0.08 and 1.68±0.05 vs. 1.36±0.13, p=0.03). Microvascular permeability in group III was reduced to 106.82±17.09 compared with 165.70±21.83 ng Evan-blue dye-gm tissue in group I (p=0.05). As shown in FIG. 12, myeloperoxidase activity in group III was significantly lower than in group I (*p=0.03). MPO=myeloperoxidase. Group III myeloperoxidase activity was 39.88±4.87 compared with 88.70±18.69 ΔOD/gm/min in group I (p=0.03), and group II myeloperoxidase activity was 56.06±7.46.

C. Conclusions

DWH-146e reduced lung neutrophil sequenstration and dramatically improved pulmonary graft function. Neutrophils are important components of the inflammatory cascade of reperfusion injury and their source may include both the circulating blood and the lung graft itself. Selective adenosine-$A_{2A}$ activation interrupts the neutrophil-mediated inflammatory response and reduces lung reperfusion injury following transplantation.

Under light microscopy, control lungs in group I showed severe leukocyte infiltration and edema formation in the alveolar spaces after 18 hours of ischemic storage and 30 minutes of reperfusion. In group II, lungs that underwent reperfusion with leukocyte-depleted blood and in group III lungs (that received DWH-146e during reperfusion, this infiltration was much less.

EXAMPLE 20

Effect of DWH-146e on Neointimal Formation after Arterial Injury

Leukocyte activation with release of inflammatory cytokines occurs after percutaneous coronary intervention and may play a role in restenosis. In the mouse, robust neointima formation in the presence of an intact endothelial lining occurs after ligation of the common carotid artery. Using this model, C57BL6 mice were randomized at the time of carotid ligation to a 7 day infusion via osmotic pump of DWH-146e, (n=7), or vehicle (n=8).

Figure 13:
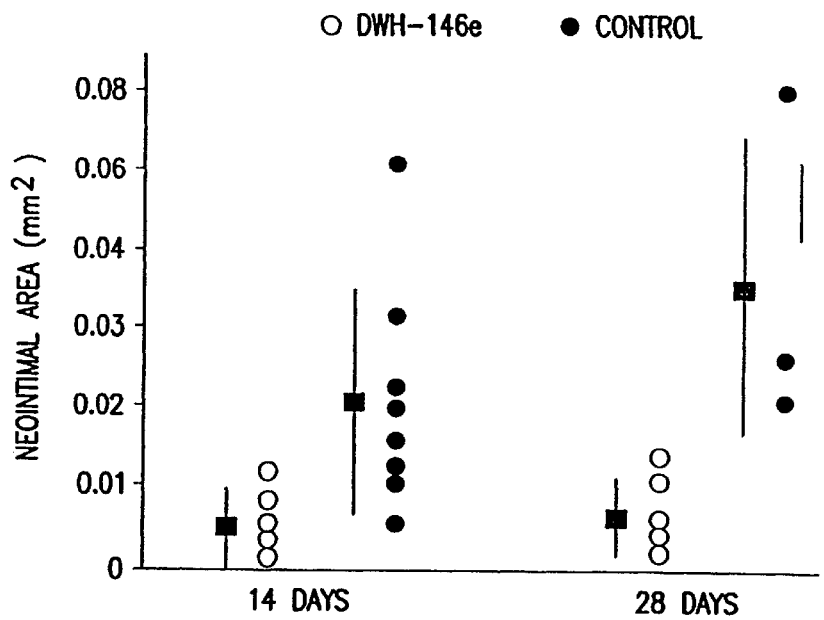
FIG. 13 is a graph depicting the effect of DWH-146e on neointimal formation after arterial injury in mice.

At 14 days after carotid ligation, histomorphometry demonstrated a significant reduction in neointimal area (0.005±0.004 mm$^2$ vs. 0.021±0.014 mm$^2$, p=0.02) and neointimal to medial area ratio (0.13±0.07 vs. 0.64±0.44, p=0.01) in the treated animals compared to controls. Medial area was similar in the two groups (0.034±0.007 mm$^2$ vs. 0.036±0.009 mm$^2$, p=0.81). This benefit in limiting neointimal growth persisted to 28 days. FIG. 13 summarizes the effect of DWH-146e to inhibit neointimal growth in the mouse LCCA model. These experiments demonstrate that, in a mouse carotid artery ligation model, prolonged $A_{2A}$ stimulation (7 days) by DWH-146e results in a significant reduction in neointimal formation for at least 21 days, possibly through its effect on leukocyte activation and function.

EXAMPLE 21

Inhibition of Endotoxin-stimulated Human Monocyte TNFα Release

A. Materials

Ficoll-hypaque was purchased from ICN (Aurora, Ohio) and Cardinal Scientific (Santa Fe, N. Mex.) and Accurate Chemicals and Scientific (Westbury, N.Y.). Endotoxin (lipopolysaccharide; *E. coli* 0111B4) was from List Biologicals (Campbell, Calif.). Hanks balanced salt solution (HBSS), and limulus amebocyte lysate assay kit were from BioWittaker (Walkersville, Md.). Human serum albumin (HSA) was from Cutter Biological (Elkhart, Ind.). ZM241385 (4-(2-[7-amino-2-(2-furyl)[1,2,4]-triazolo[2,3-a][1,3,5]triazin-5-yl amino]ethyl)phenol) was a gift from Simon Poucher, Zeneca Pharmaceuticals, Cheshire, UK.

Stock solutions (1 mM and 10 mM in DMSO) were made and stored at −20° C.

B. Production of TNFα by purified human adherent monocytes

A monocyte rich monolayer (>65% monocytes) was prepared by incubating 1 ml of the mononuclear leukocyte fraction (5×10$^5$/ml) from a Ficoll-Hypaque separation (A. Ferrante et al., *J. Immunol. Meth.*, 36, 109 (1980)) in wells of a 24 well tissue culture plate (1 hr; 37° C.; 5% CO$_2$). The non-adherent leukocytes were removed by washing and culture medium (1 ml Hanks balanced salt solution, containing 0.1% human serum albumin, adenosine deaminase [5 U/ml] and 1% heat-inactivated autologous serum) added to the wells containing the adherent mononuclear cells. As stated, the following were added: (1) endotoxin (100 ng/ml) and the A$_{2A}$ AR selective antagonist ZM241385 (100 nM) and, (2) A$_{2A}$ adenosine receptor selective agonists JMR193 (1–1000 nM), DWH146e (1–1000 nM) and CGS21680 (10–1000 nM). The samples were then incubated for 4 hours (37° C.; 5% CO$_2$) and the supernatants harvested. Any suspended cells were removed by centrifugation and the cell-free samples frozen (−70° C.). TNFα was assayed in the cell-free supernatants (n=6) by an ELISA kit (Coulter/Immunotech, Miami, Fla.).

C. Results

Figure 14:
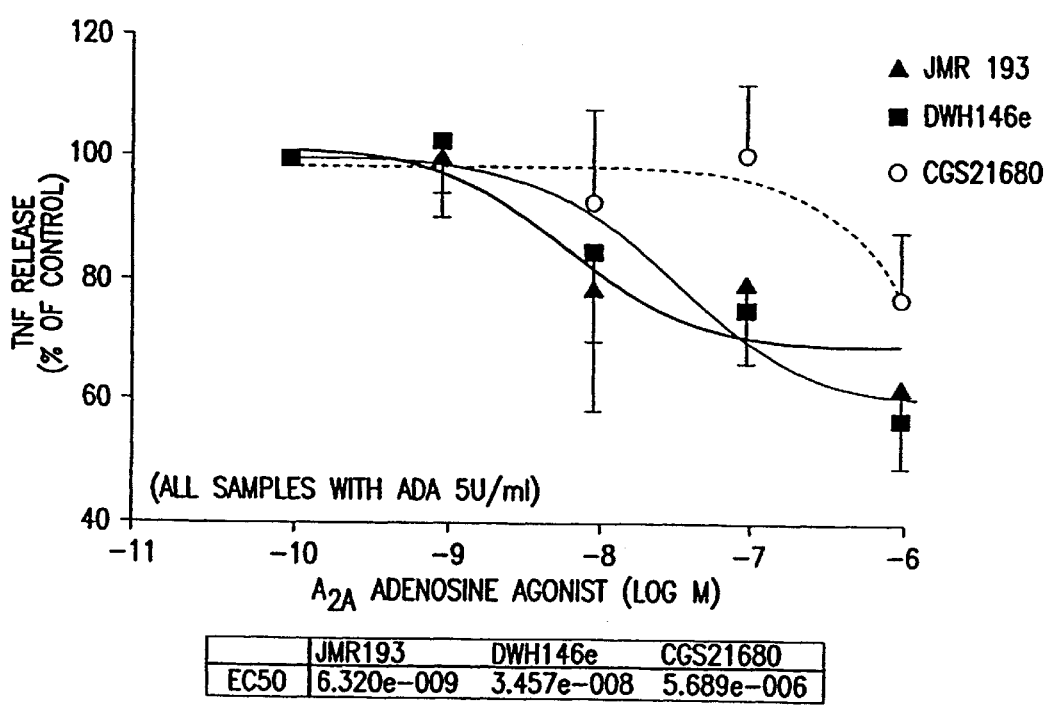
FIG. 14 is a graph depicting the effect of compounds JMR193, DWH-146e, and CGS21680 on TNF release from human monocytes.
Figure 15:
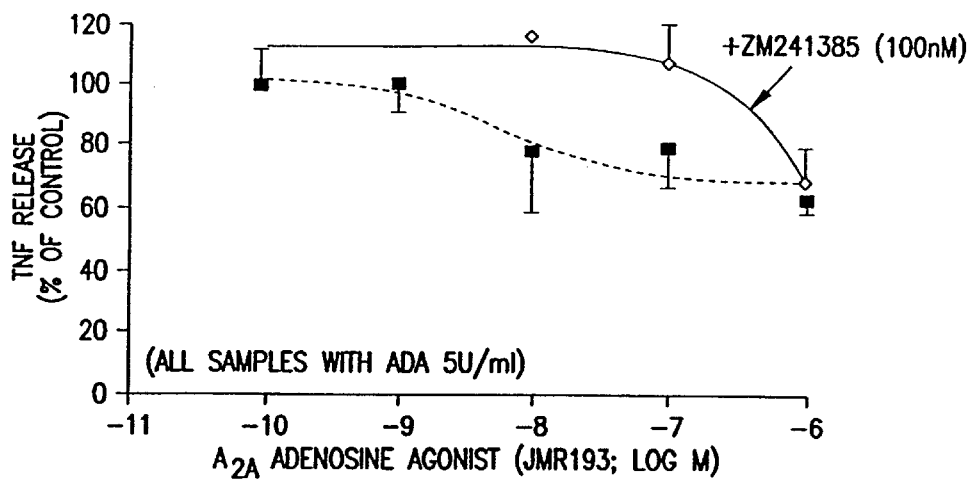
FIG. 15 is a graph depicting the effect of compound ZM241385 on the effects of JMR193 on TNF production.

As shown in FIG. 14, the A$_{2A}$ adenosine receptor agonists decreased endotoxin-stimulated adherent monocyte production of TNFα. The A$_{2A}$ AR selective antagonist ZM241385 (100 nM) antagonized the effects of JMR193 on TNFα production (FIG. 15).

Thus, DWH146e and JMR193 decrease LPS endotoxin-stimulated TNFα production by human monocytes by a mechanism that is dependent upon agonist binding to A$_{2A}$ adenosine receptors.

EXAMPLE 22

Activity of DWH-146e in Murine Peritonitis Model

Figure 16:
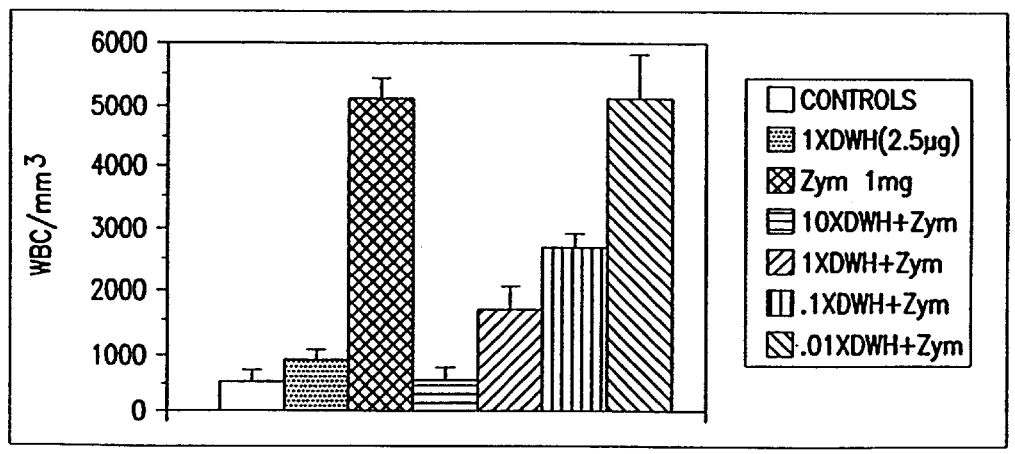
FIG. 16 is a graph depicting the activity of DWH-146e on mean leukocyte concentration (WBC/mm$^2$) in a murine peritonitis model, following injection of zymosan (Zym).

Preliminary experiments with experimental peritonitis have involved the injection of zymosan (Zym) as a potent stimulus of inflammation (Y. Zhang et al., *Eur. J. Pharmacol.*, 313, 237 (1996)). As shown in FIG. 16, following injection of zymosan, the mean leukocyte concentration as determined in a neubauer hemocytometer was 7,325±1,893/mm$^3$. Intraperitoneal injection of DWH-146e at a dosage of 2.5 μg/kg one hour prior to zymosan inhibited the development of peritonitis with a mean±SEM leukocyte concentration of 2,012±374/mm$^3$ 6 hours later (p<0.05). Thus, these studies demonstrate that the A$_{2A}$ AR is instrumental in mediating PMN traversal into the peritoneum following zymosan challenge.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of the formula (I):

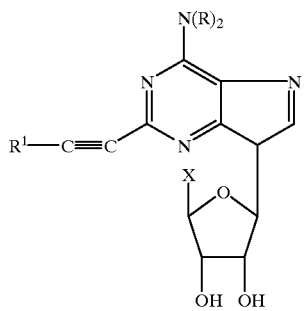

wherein (a) each R is individually hydrogen, $C_1$–$C_6$ alkyl, $C_3$–$C_7$ cycloalkyl, phenyl or phenyl($C_1$–$C_3$)-alkyl;
(b) X is —CH$_2$OH, —CO$_3$R$^2$, —OC(O)R$^2$, CH$_2$OC(O)R$^2$ or C(O)NR$^3$R$^4$;
(c) each of R$^2$, R$^3$ and R$^4$ is individually H, $C_{1-6}$-alkyl; $C_{1-6}$-alkyl substituted with 1–3 $C_{1-6}$-alkoxy, $C_3$–$C_6$ cycloalkyl, $C_{1-6}$-alkylthio, halogen, hydroxy, amino, mono($C_{1-6}$-alkyl)amino, di($C_{1-6}$-alkyl)amino, or $C_{6-10}$-aryl, wherein aryl may be substituted with 1–3 halogen, $C_{1-6}$-alkyl, hydroxy, amino, mono($C_{1-6}$-alkyl)amino, or di($C_{1-6}$-alkyl)amino; $C_{6-10}$-aryl; or $C_{6-10}$-aryl substituted with 1–3 halogen, hydroxy, amino, mono($C_{1-6}$-alkyl)amino, di($C_{1-6}$-alkyl)amino or $C_{1-6}$-alkyl;
(d) R$^1$ is (X—(Z)—)$_n$[($C_3$–$C_{10}$)cycloalkyl]-(Z')-wherein Z and Z' are individually ($C_1$–$C_6$)alkyl, optionally interrupted by 1–3 S or nonperoxide O, or are absent, and n is 1–3; or a pharmaceutically acceptable salt thereof.
2. A compound of claim 1 wherein 5'—X is CH$_2$OH or —C(O)NR$^3$R$^4$.
3. The compound of claim 2 wherein 5'—X is 13 C(O)NR$^3$R$^4$.
4. A compound of claim 3 wherein R$^3$ is H and R$^4$ is ($C_1$–$C_4$)alkyl.
5. A compound of claim 1 wherein each R is H or ($C_1$–$C_4$)alkyl.
6. A compound of claim 1 wherein Z' is —CH$_2$— or —CH$_2$—CH$_2$—.
7. A compound of claim 6 wherein Z is —CH$_2$— or —CH$_2$—CH$_2$—.
8. A compound of claim 1 wherein $C_3$–$C_{10}$ cycloalkyl is cyclohexyl or cyclopentyl.
9. A compound of claim 8 wherein X is ($C_1$–$C_4$) alkoxycarbonyl, C(O)NR$^3$R$^4$ or acetoxymethyl.
10. A compound of claim 8 wherein X—Z is HO$_2$C—Z—.
11. A compound of claim 8 wherein X—Z and Z' are trans on $C_3$–$C_{10}$ cycloalkyl.
12. A compound of claim 1 wherein R is H, 5'—X is ethylaminocarbonyl, and R$^1$—C≡C— is 2-(4-methoxycarbonyl-cyclohexylmethyl)ethynyl or 2-(4-carboxy-cyclohexylmethyl)ethynyl.
13. A compound of claim 1 wherein R is H, 5'—X is ethylaminocarbonyl, and R$^1$—C≡C— is 2-(4-acetoxymethyl-cyclohexylmethyl)ethynyl.
14. Methyl-4-(3-{9-[4S,5S,2R,3R)-5-(N-ethylcarbamoyl)-3,4-dihydroxyoxolan-2yl]-6-aminopurin-2-yl)}prop-2-ynyl)cyclohexane-carboxylate or a pharmaceutically acceptable salt thereof.
15. A therapeutic method to inhibit an inflammatory response comprising administering to a mammal in need of said therapy, an effective anti-inflammatory amount of a compound of formula (I):

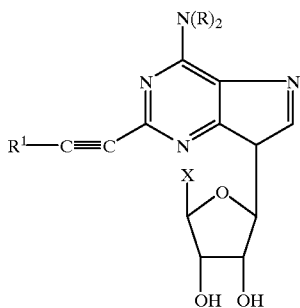

wherein
(a) each R is individually hydrogen, $C_1$–$C_6$ alkyl, $C_3$–$C_7$ cycloalkyl, phenyl or phenyl($C_1$–$C_3$)-alkyl;
(b) X is —$CH_2OH$, —$CO_2R^2$, —$OC(O)R^2$, $CH_2OC(O)R^2$ or $C(O)NR^3R^4$;
(c) each of $R^2$, $R^3$ and $R^4$ is individually H, $C_{1-6}$-alkyl; $C_{1-6}$-alkyl substituted with 1–3 $C_{1-6}$-alkoxy, $C_3$–$C_7$-cycloalkyl, $C_{1-6}$-alkylthio, halogen, hydroxy, amino, mono($C_{1-6}$-alkyl)amino, di($C_{1-6}$-alkyl)amino, or $C_{6-10}$-aryl, wherein aryl may be substituted with 1–3 halogen, $C_{1-6}$-alkyl, hydroxy, amino, mono($C_{1-6}$-alkyl)amino, or di($C_{1-6}$-alkyl)amino; $C_{6-10}$-aryl; or $C_{6-10}$-aryl substituted with 1–3 halogen, amino, mono($C_{1-6}$-alkyl) amino, di($C_{1-6}$-alkyl)amino or $C_{1-6}$-alkyl;
(d) each of $R^3$ and $R^4$ is individually hydrogen, $C_{3-7}$-cycloalkyl, or any of the meanings of $R^2$; and
(e) $R^1$ is (X—(Z)—)$_n$[($C_3$–$C_{10}$)cycloalkyl]-(Z')-wherein Z and Z' are individually ($C_1$–$C_6$)alkyl, optionally interrupted by 1–3 S or nonperoxide O, or are absent, and n is 1–3; or a pharmaceutically acceptable salt thereof.

16. The method of claim 15 wherein 5'—X is $CH_2OH$ or $C(O)NR^3R^4$.

17. The method of claim 16 wherein 5'X is —$C(O)NR^3R^4$.

18. The method of claim 17 wherein $R^3$ is H and $R^4$ is ($C_1$–$C_4$)alkyl.

19. The method of claim 15 wherein each R is H or ($C_1$–$C_4$)alkyl.

20. The method of claim 15 wherein Z' is —$CH_2$— or —$CH_2$—$CH_2$—.

21. The method of claim 19 wherein Z is —$CH_2$— or —$CH_2$—$CH_2$—.

22. The method of claim 15 wherein $C_3$–$C_{10}$ cycloalkyl comprises cyclohexyl or cyclopentyl.

23. The method of claim 22 wherein X is ($C_1$–$C_4$) alkoxycarbonyl or acetoxymethyl.

24. The method of claim 22 wherein X—Z is $HO_2C$—Z—.

25. The method of claim 22 wherein X—Z and Z' are trans on $C_3$–$C_{10}$ cycloalkyl.

26. A method of claim 15 wherein R is H, X is ethylaminocarbonyl and $R^1$—C≡C— is 2-(4-methoxycarbonyl-cyclohexylmethyl)ethynyl or 2-(4-carbonyl-cyclohexylmethyl)ethynyl.

27. A method of claim 15 wherein R is H, X is ethylaminocarbonyl, and $R^1$—C≡C— is 2-(4-acetoxymethyl-cyclohexylmethyl)ethynyl.

28. The method of claim 15 further comprising administering a Type IV phosphodiesterase inhibitor in combination with the compound of formula (I).

29. The method of claim 15 wherein rolipram is administered in combination with said compound of formula (I).

30. The method of claim 15 wherein the inflammatory response is due to ischemia.

31. The method of claim 15 wherein the inflammatory response is due to atherosclerosis.

32. The method of claim 15 wherein the inflammatory response is due to an autoimmune disease.

33. The method of claim 15 wherein the inflammatory response is due to ischemia/reperfusion injury.

34. The method of claim 15 wherein the inflammatory response is due to stroke, traumatic brain injury, or spinal cord injury.

35. The method of claim 15 wherein the inflammatory response is due to organ, tissue or cell transplantation.

36. The method of claim 15 wherein the inflammatory response is due to infection.

37. The method of claim 15 wherein the inflammatory response is due to a skin disease.

38. The method of claim 15 wherein the inflammatory response is due to angioplasty, stent placement, shunt placement or grafting.

39. The method of claim 15 wherein the inflammatory response is due to an allergic disease.

40. The method of claim 15 wherein the inflammatory response is due to a wasting disease.

41. The method of claim 15 wherein the inflammatory response is due to immunosuppressive therapy.

42. A therapeutic composition comprising a compound of claim 1 in combination with a pharmaceutically acceptable carrier.

43. The composition of claim 42 further comprising a Type IV phosphodiesterase inhibitor.

44. The composition of claim 43 wherein the inhibitor is rolipram.

45. The composition of claim 43 wherein the carrier is a liquid carrier.

46. The composition of claim 45 which is adapted for parenteral administration.

47. A method for preventing or treating a pathological condition or symptom in a mammal, wherein the activity of $A_{2A}$ adenosine receptors is implicated and agonism of such activity is desired, comprising administering to said mammal an effective amount of a compound of claim 1.

48. The method of claim 47 wherein the mammal is a human.

* * * * *

UNITED STATES PATENT AND TRADEMARK OFFICE
Certificate

Patent No. 6,232,297                                                                      Patented: May 15, 2001

On petition requesting issuance of a certificate for correction of inventorship pursuant to 35 U.S.C. 256, it has been found that the above-identified patent, through error and without deceptive intent, improperly sets forth the inventorship.

Accordingly, it is hereby certified that the correct inventorship of this patent is: Joel M. Linden, Charlottesville, VA; Gail W. Sullivan, Charlottesville, VA; Ian J. Sarembock, Charlottesville, VA; Timothy MacDonald, Charlottesville, VA; Mark Okusa, Charlottesville, VA; Irving L. Kron, Charlottesville, VA; and W. Michael Scheld, Earlysville, VA.

Signed and Sealed this Second Day of October 2001.

WILLIAM JARVIS
*Primary Examiner*
Art Unit 1614

UNITED STATES PATENT AND TRADEMARK OFFICE
CERTIFICATE OF CORRECTION

PATENT NO. : 6,232,297 B1
DATED : May 15, 2001
INVENTOR(S) : Linden et al.

It is certified that error appears in the above-identified patent and that said Letters Patent is hereby corrected as shown below:

Column 2,
Line 15, delete (TNFα)" and insert -- TNFα) --, therefor.

Column 5,
Lines 12-25, delete "

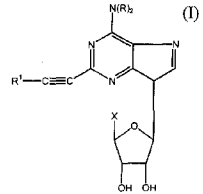

" and insert

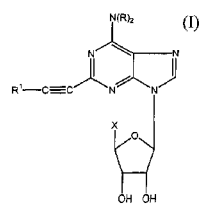

--, therefor.

Line 40, delete "(X-(Z)-$_n$[CC$_3$-C$_{10}$)" and insert -- (X-(Z)-)$_n$[(C$_3$-C$_{10}$) --, therefor.
Line 53, delete "vasaodilators" and insert -- vasodilators --, therefor.

Column 6,
Line 61, delete "thermal due" and insert -- thermal trauma due --, therefor.

Column 8,
Line 57, delete "cyclohexylmethyl;," and insert -- cyclohexylmethyl, --, therefor.

Column 9,
Line 50, delete "X = Me" and insert -- X = Me) --, therefor.

Column 10,
Line 11, delete "Deptrotection" and insert -- Deprotection --, therefor.

Column 12,
Line 60, delete "slat" and insert -- salt --, therefor.

UNITED STATES PATENT AND TRADEMARK OFFICE
CERTIFICATE OF CORRECTION

PATENT NO. : 6,232,297 B1
DATED : May 15, 2001
INVENTOR(S) : Linden et al.

It is certified that error appears in the above-identified patent and that said Letters Patent is hereby corrected as shown below:

Column 14,
Line 35, delete "produce" and insert -- product --, therefor.

Column 15,
Line 36, delete "(6,4)" and insert -- 6.4 --, therefor.

Column 16,
Line 12, delete "(4R" and insert -- (4S --, therefor.
Line 29, delete "(2R" and insert -- (2S --, therefor.
Line 56, delete "(2R" and insert -- (2S --, therefor.

Column 18,
Line 26, delete "Biological Elkhart" and insert -- Biological (Elkhart --, therefor.
Line 40, delete "separatin" and insert -- separation --, therefor.
Line 54, delete "of JMR" and insert -- or JMR --, therefor.
Lines 29-30, delete "experiments." and insert -- experiments). --, therefor.

Column 20,
Line 31, delete "give" and insert -- gives --, therefor.

Column 21,
Line 45, delete "oxygentation" and insert -- oxygenation --, therefor.
Line 48, delete "p<0.001." and insert -- p<0.001). --, therefor.

Column 22,
Line 7, delete "sequenstration" and insert -- sequestration --.
Line 21, delete "reperfusion," and insert -- reperfusion) --, therefor.
Line 33, delete "C57BL6" and insert -- C57/BL6 --, therefor.

Column 24,
Lines 5-15, delete
"
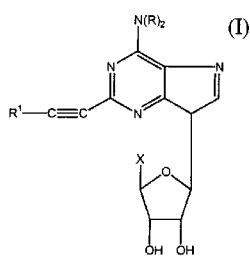
"

UNITED STATES PATENT AND TRADEMARK OFFICE
CERTIFICATE OF CORRECTION

PATENT NO. : 6,232,297 B1
DATED : May 15, 2001
INVENTOR(S) : Linden et al.

It is certified that error appears in the above-identified patent and that said Letters Patent is hereby corrected as shown below:

Column 24, cont'd.

and insert --

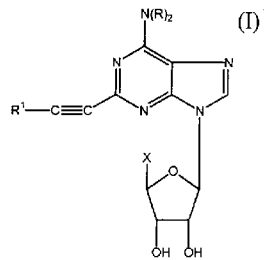

--, therefor.

Line 20, delete "-CH$_3$OH, -CO$_3$R$^2$" and insert -- CH$_2$OH, -CO$_2$R$^2$ --, therefor.
Lines 38-39, delete "13 C(O)NR$^3$R$_4$" and insert -- C(O)NR$^3$R$^4$ --, therefor.

Column 25,
Lines 3-16, delete "

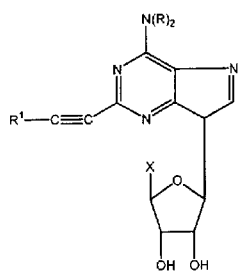

and insert --

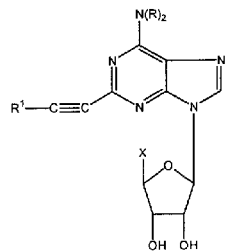

--, therefor.

UNITED STATES PATENT AND TRADEMARK OFFICE
CERTIFICATE OF CORRECTION

PATENT NO.   : 6,232,297 B1
DATED        : May 15, 2001
INVENTOR(S)  : Linden et al.

It is certified that error appears in the above-identified patent and that said Letters Patent is hereby corrected as shown below:

<u>Column 25 cont'd.</u>
Line 30, delete "halogen, amino" and insert -- halogen, hydroxy, amino --, therefor.
Line 40, delete ""5'X" and insert -- 5'-X --, therefor.

<u>Column 26,</u>
Line 4, delete "$R^{-1}$-C" and insert -- $R^1$-C-, therefor.

Signed and Sealed this

Seventh Day of January, 2003

JAMES E. ROGAN
*Director of the United States Patent and Trademark Office*